US010660605B2

United States Patent
Kang et al.

(10) Patent No.: US 10,660,605 B2
(45) Date of Patent: May 26, 2020

(54) IMAGE PROCESSING MODULE, ULTRASONIC IMAGING APPARATUS USING THE IMAGE PROCESSING MODULE, AND ULTRASONIC IMAGE GENERATION METHOD USING THE ULTRASONIC IMAGING APPARATUS

(71) Applicant: SAMSUNG ELECTRONICS CO., LTD., Suwon-si (KR)

(72) Inventors: Joo Young Kang, Yongin-si (KR); Sung Chan Park, Suwon-si (KR); Kyu Hong Kim, Seongnam-si (KR); Jung Ho Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 331 days.

(21) Appl. No.: 13/952,927

(22) Filed: Jul. 29, 2013

(65) Prior Publication Data

US 2014/0031689 A1    Jan. 30, 2014

Related U.S. Application Data

(60) Provisional application No. 61/676,548, filed on Jul. 27, 2012.

(30) Foreign Application Priority Data

Jun. 3, 2013  (KR) ........................ 10-2013-0063737

(51) Int. Cl.
*A61B 8/14* (2006.01)
*G01S 15/89* (2006.01)
(Continued)

(52) U.S. Cl.
CPC ............ *A61B 8/14* (2013.01); *G01S 7/52049* (2013.01); *G01S 15/8977* (2013.01); *G06T 5/003* (2013.01); *G06T 2207/10132* (2013.01)

(58) Field of Classification Search
None
See application file for complete search history.

(56) References Cited

U.S. PATENT DOCUMENTS 7,720,268 B2   5/2010   Slabaugh et al.
7,783,433 B2   8/2010   Gordon et al.
(Continued)

FOREIGN PATENT DOCUMENTS

CN    1600274 A     3/2005
CN    102388402 A   3/2012
(Continued)

OTHER PUBLICATIONS

Huang et al., "Ultrasound Image Reconstruction by Two-Dimensional Blind Total Variation Deconvolution", 2009 IEEE International Conferance, Dec. 9-11.*

(Continued)

*Primary Examiner* — Christopher L Cook
(74) *Attorney, Agent, or Firm* — Sughrue Mion, PLLC

(57) ABSTRACT

An image processing module includes a beamforming unit configured to provide a beamformed signal based on an input signal; a point spread function (PSF) database comprising at least one two-dimensional point spread function obtained based on at least one situational variable of the beamformed signal; and an image generation unit configured to select at least one two-dimensional point spread function from the point spread function database and perform deconvolution using the beamformed signal and the selected at least one two-dimensional point spread function to generate an image of a target portion of an object.

13 Claims, 24 Drawing Sheets

(51) Int. Cl.
*G01S 7/52* (2006.01)
*G06T 5/00* (2006.01)

(56) References Cited

U.S. PATENT DOCUMENTS

| | | | | |
|---|---|---|---|---|
| 2007/0083114 | A1* | 4/2007 | Yang | A61B 8/00 600/437 |
| 2008/0289423 | A1* | 11/2008 | Gordon | G01N 29/069 73/602 |
| 2009/0136148 | A1* | 5/2009 | Lim et al. | 382/255 |
| 2010/0054576 | A1* | 3/2010 | Tsujita | G06K 9/2018 382/134 |
| 2010/0073518 | A1* | 3/2010 | Yeh | H04N 5/217 348/231.99 |
| 2013/0090559 | A1* | 4/2013 | Park | A61B 8/5207 600/443 |
| 2013/0336597 | A1* | 12/2013 | Maeda | G06T 5/003 382/275 |
| 2014/0094702 | A1* | 4/2014 | Kim | G01N 29/0654 600/438 |

FOREIGN PATENT DOCUMENTS

| | | |
|---|---|---|
| EP | 2 159 753 B1 | 10/2010 |
| JP | 2011-35514 A | 2/2011 |
| KR | 10-2007-0092357 A | 9/2007 |
| KR | 10-0764414 B1 | 10/2007 |
| WO | 00/22573 A1 | 4/2000 |

OTHER PUBLICATIONS

Chen et al., "Three-Dimensional point spread function measurement of cone-beam computed tomography system by iterative edge-blurring algorithm", Physics in Medicine and Biology, 2004.*

Shin et al. "Sensitivity to point-spread function parameters in medical ultrasound image deconvolution", Ultrasonics, vol. 49, Mar. 2009, pp. 344-357.*

Rao et al., "Simulation of ultrasound two-dimensional array transducers using a frequency domain model", Med. Phys. 35 (7), Jul. 2008.*

Abeyratne et al., "Higher Order Versus Second Order Statistics in Ultrasound Image Deconvolution", IEEE Ultrasonics, 1997.*

Alessandrini, Martino, "StatisticalMethods for Analysis and Processing of Medical Ultrasound", Dec. 2010.*

Communication, Issued by the European Patent Office, dated Aug. 1, 2014, in counterpart European Application No. 13178349.0.

Shin et al., "Estimation of speed of sound in dual-layered media using medical ultrasound image deconvolution", Ultrasonics vol. 50, No. 7, Jun. 2010, pp. 716-725.

Shin et al., "Estimation of Average Speed of Sound Using Deconvolution of Medical Ultrasound Data", Ultrasound in Medicine and Biology vol. 36, No. 4, Apr. 2010, pp. 623-636.

Jirik et al., "Two-Dimensional Blind Bayesian Deconvolution of Medical Ultrasound Images", IEEE Transactions on Ultrasonics, Ferroelectrics, and Frequency Control vol. 55, No. 10, Oct. 2008, pp. 2140-2153.

Communication dated Dec. 27, 2016 issued by The State Intellectual Property Office of P.R. China in counterpart Chinese Application No. 201310319539.9.

Communication dated Oct. 26, 2017, issued by the European Patent Office in counterpart European Application No. 13178349.0.

Communication dated Jun. 1, 2019, issued by the Korean Patent Office in counterpart Korean Application No. 10-2013-0063737.

Shin, et al., "Estimation of Average Speed of Sound Using Deconvolution of Medical Ultrasound Data", Apr. 2010, Ultrasound in Medicinie and Biology, vol. 36, No. 4, p. 623-636, 14 pages total.

Chen and Ning, "Three-dimensional point spread function measurement of cone-beam computed tomography system by iterative edge-blurring algorithm", Apr. 29, 2004, Physics in Medicine and Biology, p. 1865-1880, 17 pages total.

Communication dated Oct. 12, 2016, issued by the European Patent Office in counterpart European Patent Application No. 13178349.0.

Communication dated Jan. 3, 2020 issued by the European Intellectual Property Office in counterpart European Application No. 13 178 349.0.

* cited by examiner

IMAGE PROCESSING MODULE, ULTRASONIC IMAGING APPARATUS USING THE IMAGE PROCESSING MODULE, AND ULTRASONIC IMAGE GENERATION METHOD USING THE ULTRASONIC IMAGING APPARATUS

CROSS-REFERENCE TO RELATED APPLICATION(S)

This application claims priority from U.S. Patent Application No. 61/676,548, filed on Jul. 27, 2012, in the U.S. Patent and Trademark Office and Korean Patent Application No. 2013-0063737, filed on Jun. 3, 2013, in the Korean Intellectual Property Office, the disclosures of which are incorporated herein by reference in their entireties.

BACKGROUND

1. Field

Apparatuses and methods consistent with exemplary embodiments relate to an image processing module, an image generation method, and an ultrasonic imaging apparatus using the same.

2. Description of the Related Art

An ultrasonic imaging apparatus emits ultrasonic waves to a specific target portion of an object such as a human body, collects an ultrasonic wave reflected by the target portion, and acquires a tomographic image of various tissues or structures within the object, for example, a tomographic image of various internal organs and soft tissues, by using information regarding the collected ultrasonic wave. The ultrasonic imaging apparatus is inexpensive, small-sized, does not emit radiation such as X-rays, and is capable of reproducing an image of an interior of an object in real time. For this reason, the ultrasonic imaging apparatus has been widely used in a field of medicine.

The ultrasonic imaging apparatus may acquire an image according to the following method. Electric signals are converted into ultrasonic waves using ultrasonic wave generation units, such as transducers, of an ultrasonic probe of the ultrasonic imaging apparatus. The converted ultrasonic waves are emitted to a target portion. Ultrasonic sensors, such as transducers, receive the ultrasonic waves reflected by the target portion and convert the received ultrasonic waves into electric signals to acquire multi-channel ultrasonic signals. Beamforming is performed on the ultrasonic signals. That is, arrival time differences among the ultrasonic signals collected by the ultrasonic sensors are corrected and a predetermined weight is added to each ultrasonic signal to emphasize a signal from a specific position and attenuate a signal from another position and the beamformed ultrasonic signals are focused. Accordingly, the ultrasonic imaging apparatus acquires an ultrasonic image based on the beamformed ultrasonic signal.

SUMMARY

One or more exemplary embodiments provide an image processing module, an image generation method, and an ultrasonic imaging apparatus using the same, in which a point spread function may be easily and simply calculated so that an ultrasonic image is promptly generated using a beamformed signal and the calculated point spread function.

One or more exemplary embodiments also provide an image processing module, an image generation method, and an ultrasonic imaging apparatus using the same, in which generation of an ultrasonic image may be promptly performed by the ultrasonic imaging apparatus by promptly and accurately selecting a point spread function, thereby generating a high-resolution ultrasonic image.

In accordance with an aspect of an exemplary embodiment, an image processing module may include a beamforming unit configured to output a beamformed signal based on an input signal, a point spread function database comprising at least one two-dimensional point spread function obtained based on at least one situational variable of the beamformed signal, and an image generation unit configured to select at least one two-dimensional point spread function from the point spread function database and perform deconvolution using the beamformed signal and the selected at least two-dimensional point spread function to generate an image of a target portion of an object. The at least one situational variable may include a sound speed of an ultrasonic wave or a location of a target portion of the object, wherein the input signal is generated in response to the ultrasonic wave emitted to the target portion of the object. The image generation unit may sort the beamformed signal based on the at least one situational variable and extract the at least one two-dimensional point spread function from the point spread function database based on a result of the sorting.

In accordance with an aspect of another exemplary embodiment, an image processing module may include a beamforming unit to output a beamformed signal based on an input signal and an image generation unit configured to estimate at least one first point spread function based on the beamformed signal, estimate a second point spread function based on the estimated at least one first point spread function, and generate an image using the beamformed signal and the estimated second point spread function to generate an image of a target portion of an object.

The image generation unit may estimate the second point spread function using the beamformed signal and the estimated at least one first point spread function. The image generation unit may estimate the second point spread function using the first point spread function and at least one second point spread function estimation variable. The at least one second point spread function estimation variable comprises at least one of a sound speed of an ultrasonic wave, a change of a sound speed thereof, a location of the target portion of the object, an arrangement form of an input signal generation module for generating the input signal, and an attenuation rate of the input signal per channel, wherein the input signal is generated in response to the ultrasonic wave emitted to the target portion of the object.

In accordance with an aspect of still another exemplary embodiment, an ultrasonic imaging apparatus may include an ultrasonic probe unit configured to emit ultrasonic waves to a target portion of an object, receive echo ultrasonic waves reflected by the target portion of the object, and convert the received echo ultrasonic waves into ultrasonic signals, a beamforming unit configured to output a beamformed ultrasonic signal based on the ultrasonic signals, and an image generation unit configured to estimate at least one point spread function based on the beamformed ultrasonic signal to generate an image. The ultrasonic imaging apparatus may further include a point spread function database including at least one point spread function for the beamformed ultrasonic signal. The ultrasonic imaging apparatus may call at least one point spread function from the point spread function database to estimate a first point spread function. The ultrasonic imaging apparatus may estimate a second point spread function using the estimated at least one first point spread function and generate an image using the beamformed ultrasonic signal and the estimated second point spread function.

In accordance with an aspect of still another exemplary embodiment, an image generation method may include emitting ultrasonic waves to a target portion of an object, receiving echo ultrasonic waves reflected by the target portion of the object, and converting the received echo ultrasonic waves into ultrasonic signals, outputting an ultrasonic signal beamformed based on the ultrasonic signals, extracting at least one point spread function from a point spread function database based on the beamformed ultrasonic signal, and generating an image from the beamformed ultrasonic signal using the at least one point spread function.

In accordance with an aspect of still another exemplary embodiment, an image generation method may include emitting ultrasonic waves to a target portion of an object, receiving echo ultrasonic waves reflected by the target portion of the object, and converting the received echo ultrasonic waves into ultrasonic signals, outputting an ultrasonic signal beamformed based on the ultrasonic signals, estimating at least one first point spread function based on the beamformed ultrasonic signal, estimating a second point spread function using the estimated at least one first point spread function, and generating an image from the beamformed signal using the estimated second point spread function.

BRIEF DESCRIPTION OF THE DRAWINGS

These and/or other aspects of the disclosure will become apparent and more readily appreciated from the following description of certain exemplary embodiments, taken in conjunction with the accompanying drawings of which.

DETAILED DESCRIPTION

Figure 1:
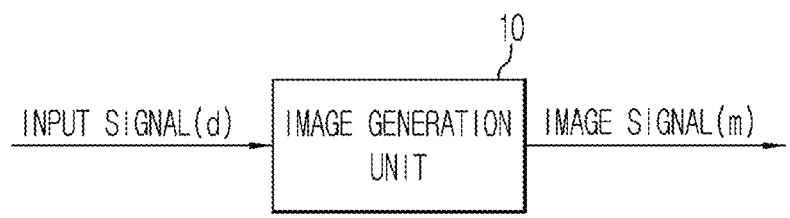
FIG. 1 is a schematic view illustrating an exemplary embodiment of an image generation unit.

Hereinafter, exemplary embodiments will now be described more fully with reference to the accompanying drawings. Like reference numerals refer to like elements throughout.

FIG. 1 is a schematic view illustrating an exemplary embodiment of an image generation unit.

As shown in FIG. 1, an image generation unit 10 generates an image signal (m) based on an input signal (d) and outputs the image signal (m). The input signal (d) may be a signal generated by a wave such as, for example, a sound wave or an electromagnetic wave. For example, in a case in which the input signal (d) is a sound wave signal, the input signal (d) may be a signal acquired from a sound wave of an audible frequency or an ultrasonic wave of a frequency greater than the audible frequency, i.e. greater than 20 kHz. On the other hand, in a case in which the input signal (d) is an electromagnetic wave signal, the input signal (d) may be a signal acquired from a microwave (having a wavelength of about 10 cm to about 100 cm) used in a radar, etc.

To generate the image signal (m) from the input signal (d), the image generation unit 10 estimates at least one point spread function (PSF) and performs deconvolution using the estimated result to generate and acquire an image identical to or substantially approximate to an original object which is photographed. The image generation unit 10 outputs the generated and acquired image in a form of the image signal (m).

The point spread function is a function which is related to image data acquired through an image photographing apparatus to generate final image data. The point spread function is mainly used to restore ideal image data.

Figure 2:
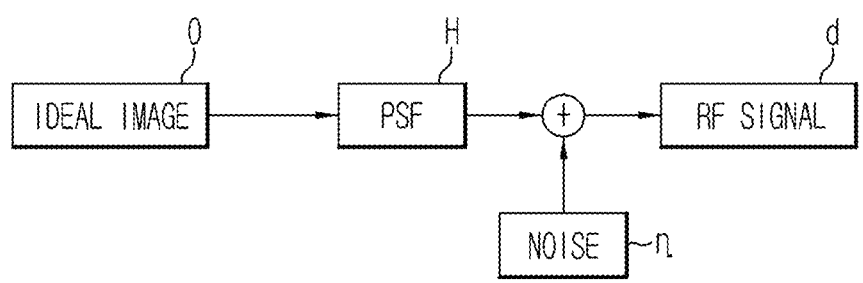
FIG. 2 is a view for explaining a point spread function.

FIG. 2 is a view for explaining a point spread function H. As shown in FIG. 2, when obtaining an image of an object through the image photographing apparatus, the image photographing apparatus may output a signal, for example, an RF signal (d) such as an ultrasonic signal from an ultrasonic imaging apparatus by using the point spread function H. In this case, the RF signal (d) may be different from an ideal image o due to technical or physical characteristics of the image photographing apparatus or noise η introduced therein.

In other words, the RF signal (d), which is acquired by the image photographing apparatus, may be deformed from an ideal image due to the technical or physical characteristics of the image photographing apparatus and noise η added thereto.

Figure 3:
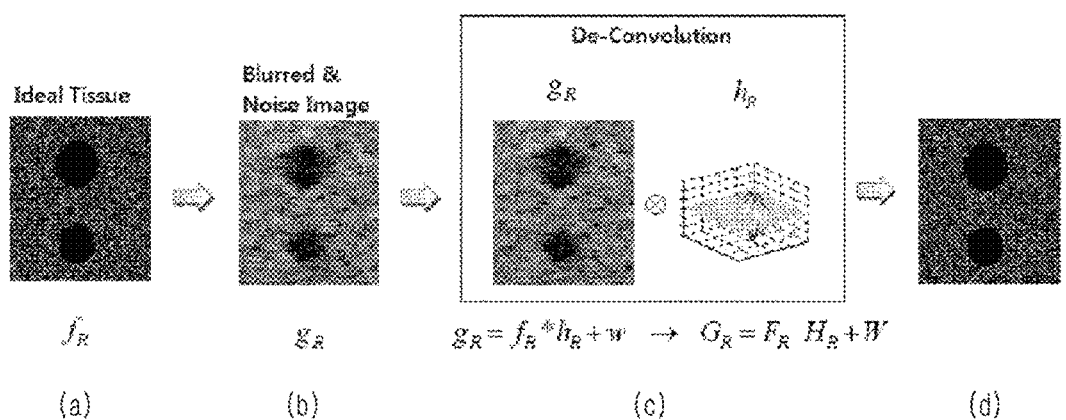
FIG. 3 is a view for explaining a relationship between an ideal image, a radio frequency (RF) image, and deconvolution.

FIG. 3 is a view for explaining a relationship between an ideal image, and an RF image, and deconvolution in an ultrasonic imaging apparatus. FIG. 3(a) shows an ideal image $f_R$ of tissues of a human being and FIG. 3(b) shows an ultrasonic image $g_R$ collected by an ultrasonic probe of the ultrasonic imaging apparatus and beamformed. That is, the ideal image $f_R$ is different from the RF image $g_R$, which will be described in more detail with reference to FIGS. 4A to 4C.

Figure 4A:
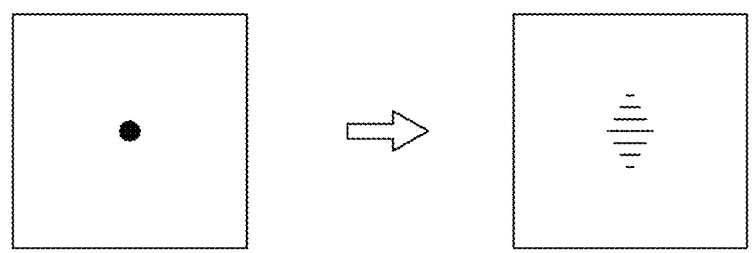
FIG. 4A is a view for explaining a relationship between an ideal image and an RF image.

FIG. 4A is a view for explaining a relationship between an ideal image and an RF image. An image based on an input signal shown in FIG. 4A is an example of an ultrasonic image acquired using the ultrasonic imaging apparatus. An ideal image o of a target portion ob1 in an ideal state is shown in a left part of FIG. 4A, an image of the target portion ob1 based on an input signal (d), such as an RF signal, is shown in a right part of FIG. 4A. Specifically, the target portion ob1 in the image based on the input signal (d) is displayed as if the target portion ob1 in the ideal image were widened vertically and horizontally. That is, the image based on the input signal is significantly different from the ideal image. In a case in which the image based on the input signal (d), i.e. the RF signal, is restored without change, the object appears to be different from an actual shape thereof.

Figure 4B:
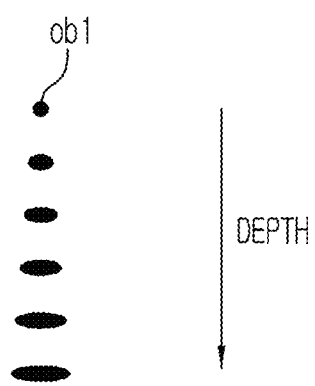
FIG. 4B is a view showing an example of an ultrasonic image of a target portion based on an RF signal according to a depth of a target portion.

The image based on the input signal (d) may be further deformed from the ideal image according to a distance therebetween. FIG. 4B is a view showing an example of an ultrasonic image of the target portion based on an RF signal according to a depth of the target portion and FIG. 4C is a view showing an example of an ultrasonic image of a target portion according to a depth of the target portion.

Figure 4C:
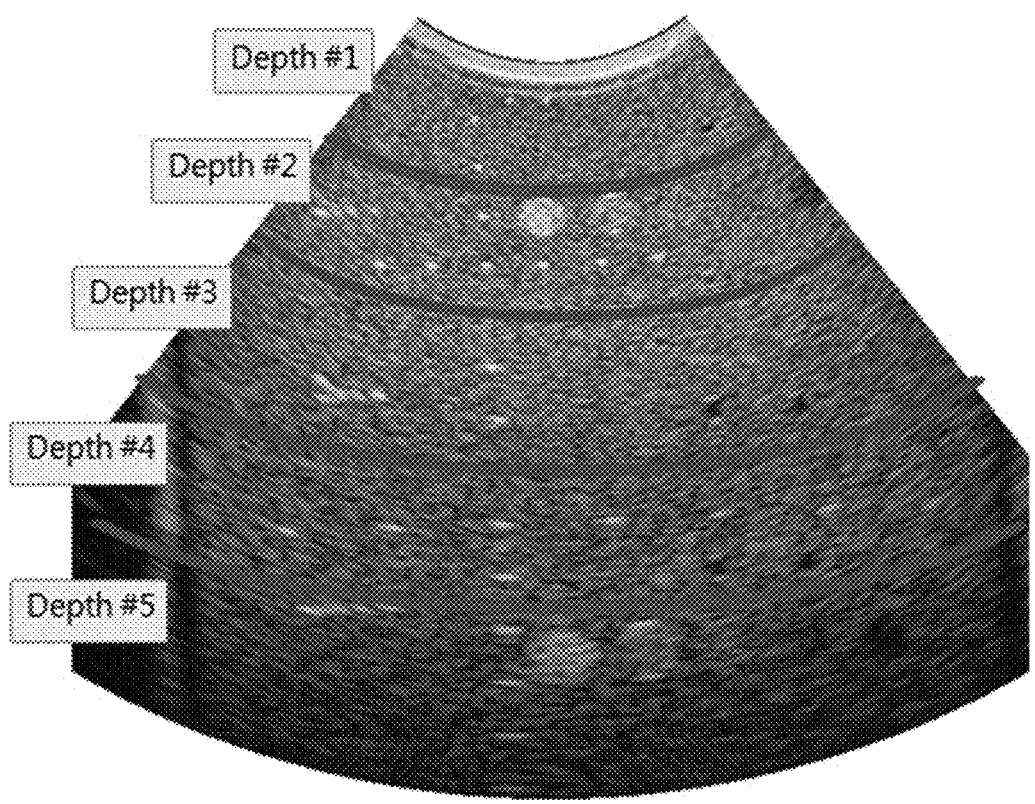
FIG. 4C is a view showing an example of an ultrasonic image of a target portion according to a depth of the target portion.

If a distance between the target portion ob1 and an image data collection unit, such as an ultrasonic probe unit, is relatively short as shown in FIG. 4B, for example, in a case where a lesion in a human body is located at a first depth (depth #1) as shown in FIG. 4C, an image of the target portion ob1 based on the input signal is equal or substantially similar to an ideal image of the same object. On the other hand, if the distance between the target portion ob1 and the image data collection unit is relatively long, for example, in a case where a lesion in a human body is located at a fourth or fifth depth (depth #4 or depth #5) as shown in FIG. 4C, an image of the target portion ob1 based on the input signal (d) is widened in a lateral direction and thus becomes significantly different from the ideal image of the target portion ob1. That is, an image of the target portion ob1 in the image based on the input signal may be further deformed from the ideal image of the target portion ob1 in shape according to the distance between the data collection unit and the target portion ob1.

In a case in which the ideal image o is restored using the RF signal (d), the difference between the ideal image o and the image based on the RF signal (d) may be corrected to obtain an improved image of the target portion ob1. In this case, the RF signal (d) is corrected using a predetermined function to restore an image based on the premise that the ideal image o and the acquired RF signal (d) have a predetermined relationship therebetween. In an exemplary embodiment, the predetermined function may be a point spread function H.

A relationship between the ideal image o, the point spread function H, the noise η, and the input signal (d), i.e. the RF signal, may be represented by Equation 1.

$$d = Hf + \eta \quad \text{[Equation 1]}$$

Herein, d represents an output RF signal, H represents a point spread function, f represents a signal for an ideal image, and η represents noise.

If noise is absent, the RF signal (d) may be represented by the product of the ideal image o and the point spread function H. If a point spread function H adapted to the measured RF signal (d) is known, the ideal image o corresponding to the measured RF signal (d) may be obtained. In other words, if the point spread function H and the RF signal (d) are known, an image identical or substantially approximate to the object may be restored.

The image generation unit 10 generates an image identical or substantially similar to the ideal image o using the RF signal, i.e. the input signal (d), and the point spread function H adapted to the input signal (d) and outputs an image signal (m) corresponding to the generated image. Thus, the RF signal (d) is restored to the ideal image. In other words, the image generation unit 10 adds and synthesizes a point spread function $h_R$ adapted to an RF signal $g_R$ through deconvolution as shown in FIG. 3(c) to generate a restored image identical to or substantially approximate to an ideal image o, $f_R$.

To restore an image identical to or substantially approximate to the object based on the input signal (d), the image generation unit 10 estimates a point spread function without lowering of resolution in various directions using a point spread function (PSF) database 12 including one-dimensional or two-dimensional point spread function or using a method of estimating a two-dimensional point spread function based on a one-dimensional point spread function.

The image generation unit 10 converts the input signal (d), such as the RF signal, acquired by photographing the object using the estimated point spread function H such that an image based on the input signal (d) has a form or a shape identical or substantially similar to that of the target object. That is, the image generation unit 10 restores an image of the target object based on the input signal (d) acquired using the point spread function and outputs an image signal (m) corresponding to the restored image.

Figure 5:
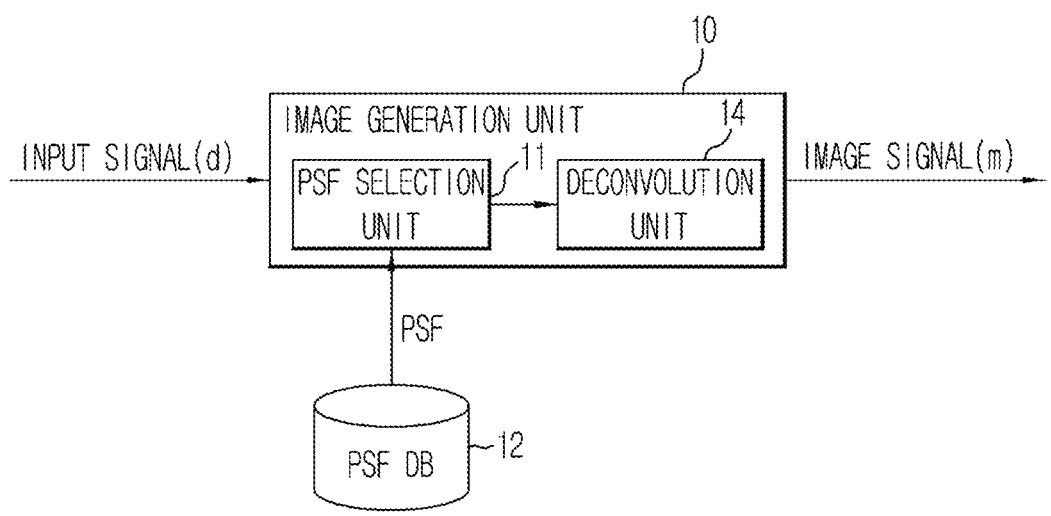
FIG. 5 is a block diagram illustrating an exemplary embodiment of an image generation unit.

FIG. 5 is a block diagram illustrating an exemplary embodiment of an image generation unit.

As shown in FIG. 5, the image generation unit 10 may include a point spread function selection unit 11 and a deconvolution unit 14.

Figure 6:
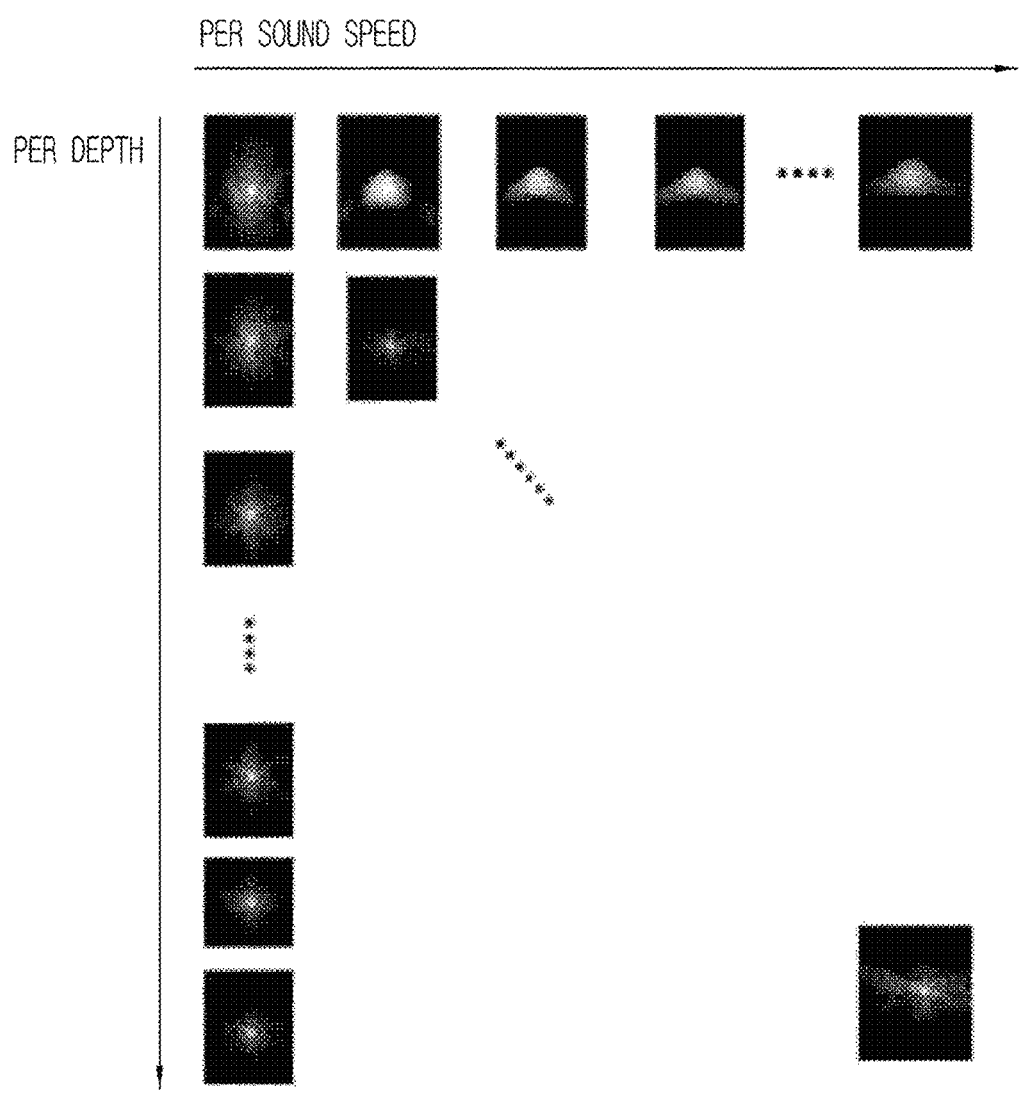
FIG. 6 is a view illustrating an exemplary embodiment of point spread functions included in a point spread function database.

The point spread function selection unit 11 retrieves the point spread function database 12 to select and call at least one point spread function from the point spread function database 12. FIG. 6 is a view illustrating an exemplary embodiment of point spread functions included in a point spread function database. As shown in FIG. 6, the point spread function database 12 includes at least one set of point spread functions.

In an exemplary embodiment, the point spread function database 12 may include only one-dimensional point spread functions or only two-dimensional point spread functions. Alternatively, the point spread function database 12 may include both the one-dimensional point spread functions and the two-dimensional point spread functions. In another exemplary embodiment, the point spread function database 12 may include higher dimensional point spread functions, such as three-dimensional or four-dimensional point spread functions.

The point spread functions stored in the point spread function database 12 may be pre-calculated based on at least one circumstantial variable. In an exemplary embodiment, the circumstantial variable may be a speed of a wave (a horizontal axis of FIG. 6). The speed of the wave may be a speed (a sound speed) of a sound wave, such as an ultrasonic wave. In another exemplary embodiment, the circumstantial variable may be a distance between a data collection unit, such as an ultrasonic probe unit, and a target portion (a vertical axis of FIG. 6). For example, the distance between the data collection unit and the target portion may be a depth of a specific target portion, such as a lesion, in a human body.

It should be noted that the point spread functions stored in the point spread function database 12 may be pre-calculated based on two circumstantial variables. In this case, the two circumstantial variables may be a sound speed and a depth of a target portion from the data collection unit as shown in FIG. 6. In other words, as shown in FIG. 6, the point spread function database 12 may include sets of point spread functions respectively acquired according to circumstantial variables, such as a sound speed and a depth of the target portion.

To promptly estimate two-dimensional point spread functions, the point spread function database 12 may include at least one two-dimensional point spread function acquired through real measurement according to various circumstantial variables, such as a speed of an ultrasonic wave and a depth of a target portion ob1, based on the assumption that one-dimensional point spread functions in an axial direction are similar to each other, which will hereinafter be described.

The point spread function selection unit 11 selects at least one point spread function from the point spread function database 12 configured as described above. In an exemplary embodiment, the point spread function selection unit 11 may select a two-dimensional (2D) point spread function from the point spread function database 12.

In this case, the point spread function selection unit 11 may select at least one point spread function according to an input signal (d). If a target portion ob1 is located at a place which is not relatively deep in a human body, for example, a first depth of FIG. 4C, the point spread function selection unit 11 selects a point spread function corresponding to the first depth from the point spread function database 12. In a case in which a target portion ob1 at the fourth depth or the fifth depth of FIG. 4C is photographed, the point spread function selection unit 11 selects a point spread function corresponding to the fourth depth or the fifth depth from the point spread function database 12.

The point spread function selection unit 11 transmits the selected point spread function or information regarding the selected point spread function to the deconvolution unit 14.

The deconvolution unit 14 deconvolutes the input signal (d) using the point spread function selected by the point spread function selection unit 11. Consequently, an image signal (m) identical to or substantially approximate to the ideal image o is acquired from the input signal (d), i.e. the RF signal (d) shown in FIG. 2.

In a case in which the point spread function selection unit 11 selects a two-dimensional point spread function from the point spread function database 12, the deconvolution unit 14 two-dimensionally deconvolutes the input signal (d) based on the selected two-dimensional point spread function. In a case in which the point spread function selection unit 11 selects a one-dimensional point spread function from the point spread function database 12, the deconvolution unit 14 may one-dimensionally deconvolute the input signal (d).

Consequently, the image generation unit 10 may generate an image identical or substantially similar to the ideal image o from the input signal (d). The generated image is output as an image signal (m).

As described above, the image generation unit 10 may select at least one two-dimensional point spread function from the point spread function database 12 according to the input signal (d) and deconvolute the input signal (d) using the selected two-dimensional point spread function to generate an image identical or substantially similar to the ideal image o based on the input signal (d).

As shown in FIG. 2 and Equation 1, in a process of acquiring the ideal image o from the RF signal (d), an inverse function of a point spread function is calculated. In a case in which the point spread function is two-dimensional, a complexity in calculation is increased when calculating an inverse function of the two-dimensional point spread function.

In a case in which a one-dimensional point spread function is used, a computational load is decreased. However, a resolution of a specific region is lowered due to limitations of the one-dimensional point spread function. In one direction, for example, in a vertical direction, a resolution may not be lowered. In another direction, for example, in a horizontal direction, a resolution may be lowered.

In an exemplary embodiment, the image generation unit 10 selects a two-dimensional point spread function adapted to the input signal (d) from the point spread function database 12 and performs two-dimensional deconvolution using the selected two-dimensional point spread function. Consequently, a complex calculation process of acquiring an inverse function may be avoided, thereby reducing a complexity in restoring an image and improving resolution.

Figure 7:
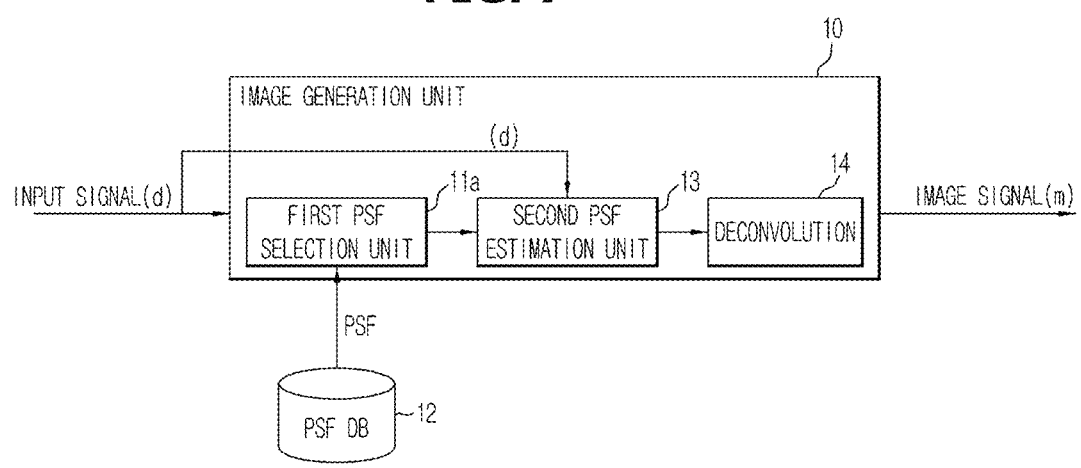
FIG. 7 is a block diagram illustrating another exemplary embodiment of an image generation unit.

FIG. 7 is a block diagram illustrating another exemplary embodiment of an image generation unit.

As shown in FIG. 7, the image generation unit 10 may include a first point spread function selection unit 11a, a second point spread function estimation unit 13, and a deconvolution unit 14.

In a manner similar to the point spread function selection unit 11 as described above, the first point spread function selection unit 11a may select at least one point spread function from an additional point spread function database 12 and transmit the selected point spread function to the second point spread function estimation unit 13.

In an exemplary embodiment, the point spread function database 12 may include one-dimensional point spread functions pre-calculated based on at least one circumstantial variable. For example, as shown in FIG. 4C, the point spread function database 12 may include point spread functions respectively acquired according to circumstantial variables, such as a sound speed of an ultrasonic wave and a depth of the target portion.

In an exemplary embodiment, the first point spread function selection unit 11a may select at least one one-dimensional point spread function from the point spread function database 12.

In this case, to promptly estimate a two-dimensional point spread function, the first point spread function selection unit 11a may select the one-dimensional point spread function in a lateral direction according to various circumstantial variables, such as a speed of an ultrasonic wave and a depth of a target portion ob1, based on the assumption that one-dimensional point spread functions in an axial direction are substantially similar to each other. The one-dimensional point spread function selected by the first point spread function selection unit 11a is transmitted to the second point spread function estimation unit 13.

The second point spread function estimation unit 13 estimates a two-dimensional point spread function using the received one-dimensional point spread function. Here, the point spread function transmitted to the second point spread function estimation unit 13 may be a one-dimensional point spread function in a lateral direction.

One-dimensional point spread functions may be divided in an axial direction or in a lateral direction. One-dimensional point spread functions in an axial direction are substantially approximate to each other based on a depth of the target portion or a sound speed of an ultrasonic wave.

Figure 8:
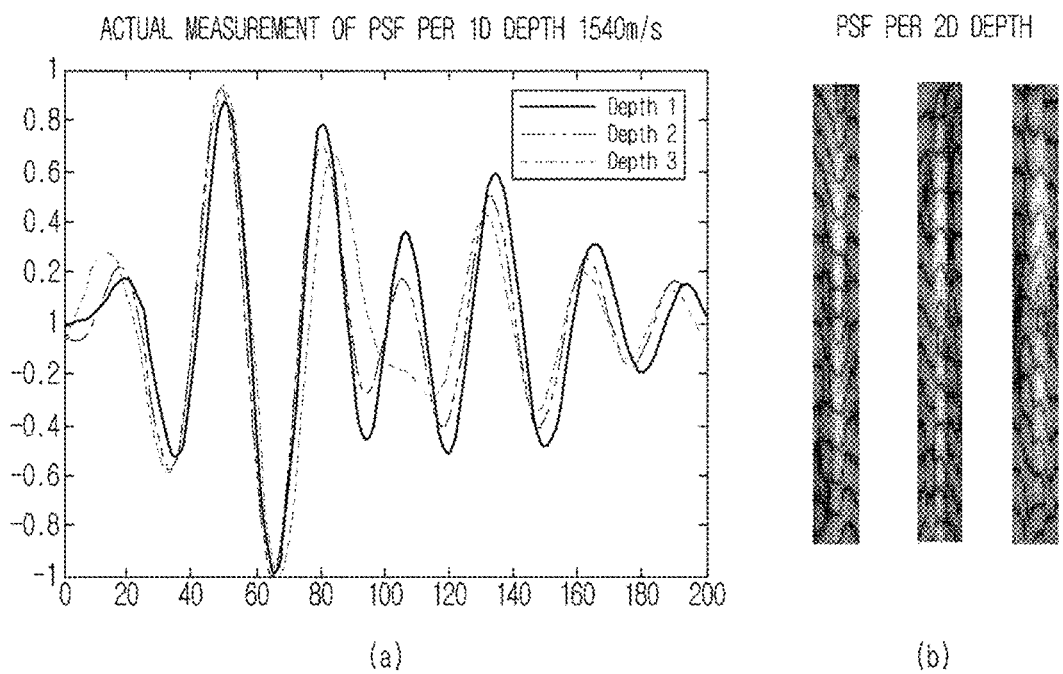
FIGS. 8 and 9 are views illustrating a point spread function measured according to a sound speed of an ultrasonic wave and a depth of a target portion.
Figure 9:
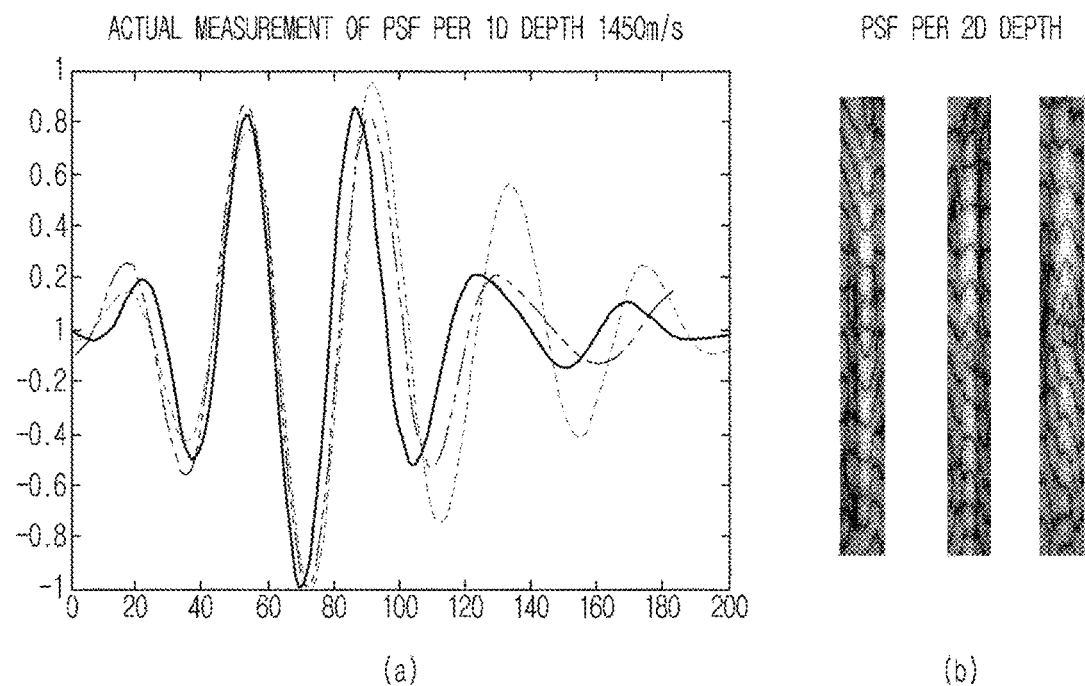

FIGS. 8 and 9 are views illustrating a point spread function measured according to sound speed of an ultrasonic wave and a depth of a target portion. FIGS. 8(a) and 9(a) show an example of one-dimensional point spread functions (1D PSF) used in the ultrasonic imaging apparatus in the form of a graph. FIG. 8(a) is a graph showing one-dimensional point spread functions of an ultrasonic wave acquired by emitting the ultrasonic wave to three target portions having different depths in a case in which the ultrasonic wave has a sound speed of 1540 m/s. FIG. 9(a) is a graph showing one-dimensional point spread functions of an ultrasonic wave acquired by emitting the ultrasonic wave to three target portions having different depths in a case in which the ultrasonic wave has a sound speed of 1450 m/s.

As shown in FIGS. 8(a) and 9(a), the one-dimensional point spread functions are substantially similar in shape to each other although the sound speeds of the ultrasonic waves are different from each other. Furthermore, the one-dimensional point spread functions have substantially similar patterns even in a case in which the depths of the target portions are different from each other (depth 1 to depth 3).

Thus, the one-dimensional point spread functions are substantially similar to each other in shape although the sound speeds of the ultrasonic waves are different from each other and the depths of the target portions are different from each other.

Two-dimensional point spread functions based on a depth of the target portion are shown in FIGS. 8(b) and 9(b). Unlike the one-dimensional point spread functions shown in FIGS. 8(a) and 9(a), the two-dimensional point spread functions are very different from each other according to depth of the target portion. That is, the point spread functions in the lateral direction have different shapes according to a depth of the target portion or a sound speed of an ultrasonic wave, unlike the point spread functions in the axial direction.

Since the one-dimensional point spread functions in the axial direction are not significantly changed according to a sound speed of an ultrasonic wave or a depth of a target portion, the second point spread function estimation unit 13 may estimate a two-dimensional point spread function based on the one-dimensional point spread function in the lateral direction selected by the first point spread function selection unit 11a using a calculation method based on the assumption that the one-dimensional point spread functions in the axial direction are substantially uniform.

In an exemplary embodiment, the second point spread function estimation unit 13 may estimate a two-dimensional point spread function considering characteristics of the input signal (d), pre-input setting, or various kinds of variables, such as a second point spread function estimation variable, as well as the one-dimensional point spread function in the lateral direction selected by the first point spread function selection unit 11a.

For example, the second point spread function estimation variable used in the second point spread function estimation unit 13 may be a beamforming coefficient used to beamform the input signal (d).

In a case in which the second point spread function estimation variable is applied to an ultrasonic imaging apparatus, the second point spread function estimation variable may be a variable such as, for example, a sound speed of an ultrasonic wave, change of a sound speed, a distance of a target portion in an object from the ultrasonic imaging apparatus, an arrangement form of an input signal generation module for generating the input signal, or an attenuation rate of an input signal per channel. The second point spread function estimation unit 13 may estimate a more correct two-dimensional point spread function using the second point spread function estimation variable.

The deconvolution unit 14 performs deconvolution using the estimated two-dimensional point spread function to generate and output an image signal (m).

The image generation unit 10 may select at least one one-dimensional point spread function from the point spread function database 12 according to the input signal (d), estimate a two-dimensional point spread function based on the selected one-dimensional point spread function, and perform deconvolution according to the estimated two-dimensional point spread function to generate an image identical or substantially similar to the ideal image o based on the input signal (d).

Figure 10:
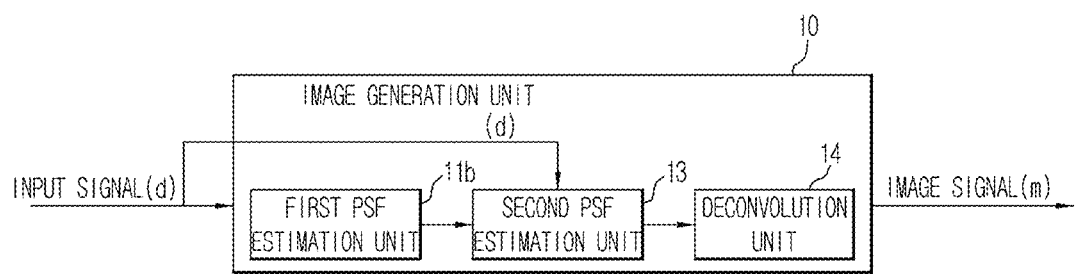
FIG. 10 is a block diagram illustrating still another exemplary embodiment of an image generation unit.

FIG. 10 is a block diagram illustrating still another exemplary embodiment of an image generation unit.

As shown in FIG. 10, the image generation unit 10 may include a first point spread function estimation unit 11b, a second point spread function estimation unit 13, and a deconvolution unit 14.

The first point spread function estimation unit 11b may estimate an appropriate one-dimensional point spread function based on an input signal (d). In a case in which a one-dimensional point spread function is estimated, a fewer variables of the input signal (d) are considered than in a case in which a two-dimensional point spread function is estimated. Accordingly, a computational load required to decide a point spread function is decreased compared with when directly estimating a two-dimensional point spread function.

In an exemplary embodiment, the first point spread function estimation unit 11b may estimate a point spread function in one direction or in a plurality of directions. Alternatively, the first point spread function estimation unit 11b may estimate point spread functions in one direction or in a plurality of directions.

In an exemplary embodiment, the first point spread function estimation unit 11b may estimate a first point spread function using at least one filter. In this case, the filter may be a least square filter (LSF) such as, for example, a minimum least square filter or a cepstrum filter.

In an exemplary embodiment, the first point spread function estimation unit 11b may estimate a point spread function in a lateral direction.

The second point spread function estimation unit 13 estimates a second point spread function using the first point spread function estimated by the first point spread function estimation unit 11b.

In an exemplary embodiment, the second point spread function estimation unit 13 may estimate a two-dimensional point spread function based on a point spread function in a lateral direction estimated by the first point spread function estimation unit 11b using a calculation method based on the assumption that point spread functions in an axial direction are substantially uniform according to a sound speed of an ultrasonic wave and a depth of a target portion, as described above with reference to FIGS. 8 and 9.

As shown in FIG. 10, the second point spread function estimation unit 13 may estimate a second point spread function considering characteristics of the input signal (d), pre-input setting, or various kinds of variables as well as the one-dimensional point spread function in the lateral direction selected by the first point spread function selection unit 11a.

In the same manner as described above, the second point spread function estimation unit 13 may estimate a second point spread function using a beamforming coefficient. Furthermore, in a case in which the second point spread function estimation unit 13 is used in an ultrasonic imaging apparatus, the second point spread function estimation unit 13 may estimate a second point spread function using another variable, such as a sound speed of an ultrasonic wave or a distance of a target portion in an object from the ultrasonic imaging apparatus.

The deconvolution unit 14 performs deconvolution using the estimated two-dimensional point spread function to generate and output an image signal (m).

As described above, the image generation unit 10 may estimate at least one one-dimensional point spread function according to the input signal (d) without retrieval data from an additional database, estimate a two-dimensional point spread function based on the estimated one-dimensional point spread function, and deconvolute the input signal (d) using the estimated two-dimensional point spread function to restore an image identical or substantially similar to the ideal image o based on the input signal (d).

Hereinafter, an exemplary embodiment of an ultrasonic imaging apparatus will be described with reference to FIGS. 11 to 18.

Figure 11:
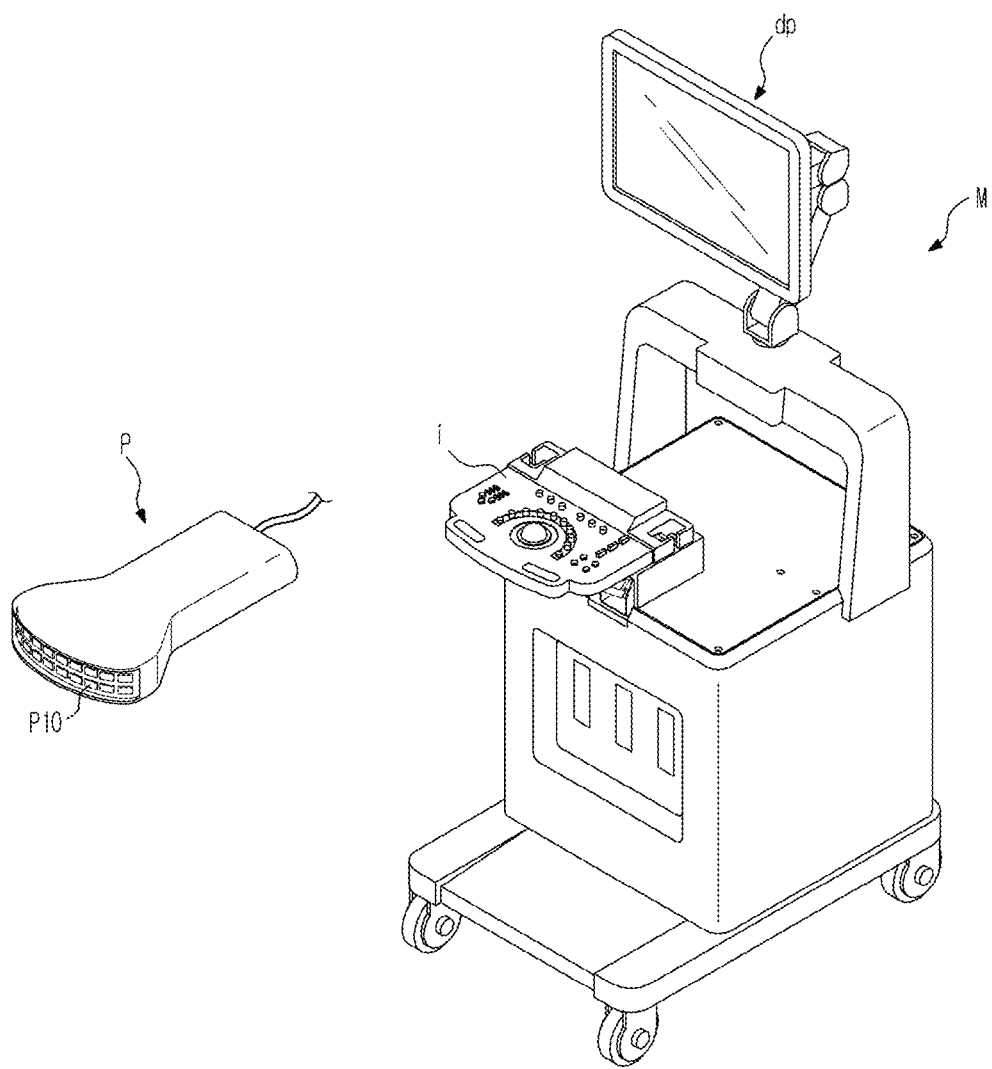
FIG. 11 is a perspective view illustrating an exemplary embodiment of an ultrasonic imaging apparatus.
Figure 12:
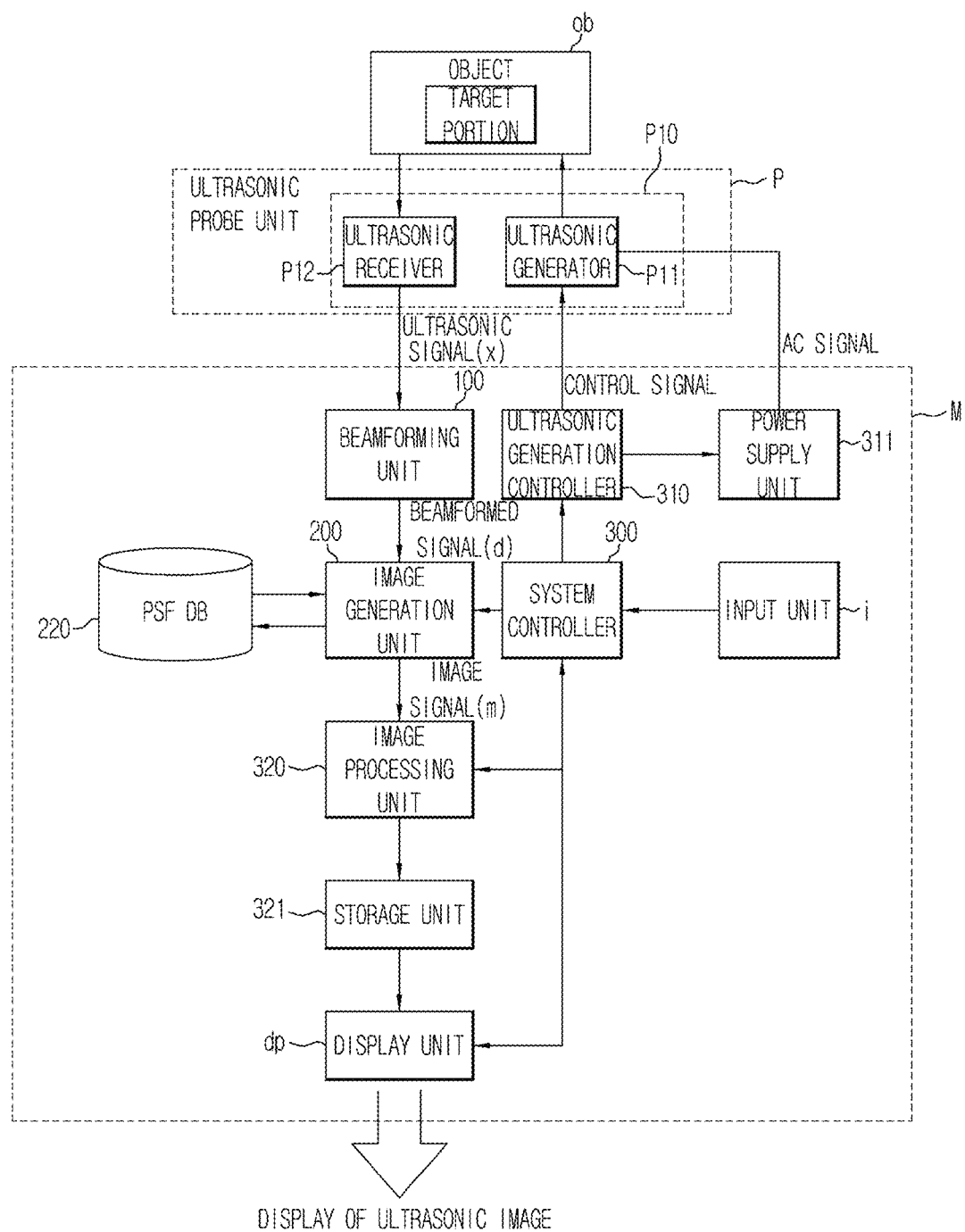
FIG. 12 is a block diagram illustrating an exemplary embodiment of an ultrasonic imaging apparatus.

FIG. 11 is a perspective view illustrating an exemplary embodiment of an ultrasonic imaging apparatus and FIG. 12 is a block diagram illustrating an exemplary embodiment of the ultrasonic imaging apparatus. As shown in FIGS. 11 and 12, the ultrasonic imaging apparatus includes an ultrasonic probe unit P to collect an ultrasonic signal with respect to an interior of an object ob and a main body M of the object ob to generate an ultrasonic image from the ultrasonic signal collected by the ultrasonic probe unit P.

The ultrasonic probe unit P may include an ultrasonic generator P11 to generate an ultrasonic wave based on applied power and to emit the generated ultrasonic wave to a target portion ob1 in the object ob and an ultrasonic receiver P12 to receive an echo ultrasonic wave reflected by the target portion ob1 of the object ob to convert the received echo ultrasonic wave into an electric signal.

The ultrasonic generator P11 is vibrated according to a pulse signal or AC current applied to the ultrasonic generator P11 to generate an ultrasonic wave under control of an ultrasonic generation controller 310 installed in the main body M.

The ultrasonic wave generated by the ultrasonic generator P11 is reflected by the target portion ob1 in the object. The ultrasonic receiver P12 receives an echo ultrasonic wave and is vibrated according to a frequency of the received echo ultrasonic wave to convert the received echo ultrasonic wave into a predetermined electric signal. As a result, the ultrasonic receiver P12 may output an ultrasonic signal (x). In a case in which the ultrasonic imaging apparatus is coupled to a photoacoustic imaging apparatus, the ultrasonic receiver P12 may receive a sound wave, such as an ultrasonic wave, generated from the target portion ob1 due to emission of laser.

Figure 13:
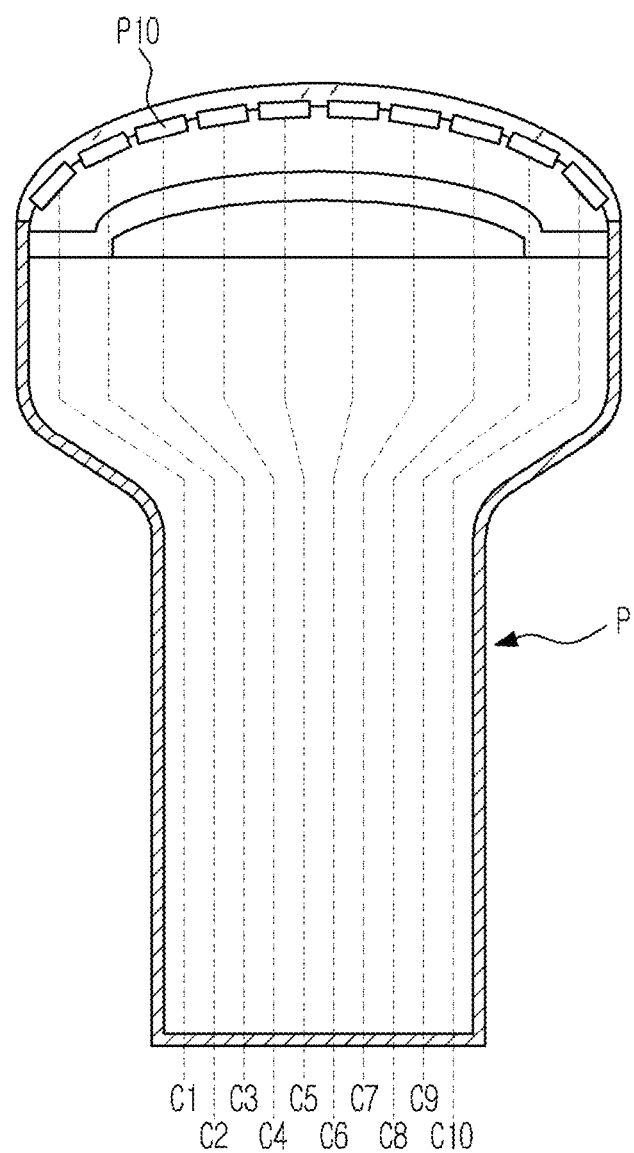
FIG. 13 is a plan view illustrating an exemplary embodiment of an ultrasonic probe unit.

The functions of the ultrasonic generator P11 and the ultrasonic receiver P12 may be performed by an ultrasonic transducer P10 disposed at one end of the ultrasonic probe unit P. FIG. 13 is a plan view illustrating an exemplary embodiment of an ultrasonic probe unit. As shown in FIG. 13, the ultrasonic transducer P10 is installed at one end of the ultrasonic probe unit P.

A transducer is a device to convert one form of energy, such as electric energy, into another form of energy, such as wave energy or light energy. The ultrasonic transducer P10 performs conversion between wave energy and electric energy. Specifically, the ultrasonic transducer P10 is vibrated according to a predetermined pulse current input thereto to generate an ultrasonic wave. In addition, the ultrasonic transducer P10 is vibrated according to an ultrasonic wave received from the outside, such as an echo ultrasonic wave, to generate an electric signal of a predetermined pulse (hereinafter, referred to as an ultrasonic signal). Consequently, the ultrasonic transducer P10 may perform the functions of the ultrasonic generator P11 and the ultrasonic receiver P12.

More specifically, the ultrasonic transducer P10 receives AC current from a power supply unit 311 such as an external power supply device or an internal electricity storage device, for example, a battery, and a piezoelectric vibrator or a thin film of the ultrasonic transducer P10 is vibrated according to the applied AC current to generate an ultrasonic wave. On the other hand, the piezoelectric vibrator or the thin film of the ultrasonic transducer P10 is vibrated by a received ultrasonic wave to generate AC current of a frequency of the vibration frequency, thereby converting the ultrasonic wave into an ultrasonic signal. As shown in FIGS. 12 and 13, the converted ultrasonic signal is transmitted to a beamforming unit 100 of the main body M through a plurality of channels c1 to c10.

As shown in FIG. 13, a plurality of ultrasonic transducers P10 may be installed at one end of the ultrasonic probe unit P. For example, 64 or 128 ultrasonic transducers P10 may be installed at one end of the ultrasonic probe unit P. In a case in which a plurality of ultrasonic transducers P10 is installed at one end of the ultrasonic probe unit P, ultrasonic signals are transmitted to the beamforming unit 100 through a plurality of channels corresponding to the number of the ultrasonic transducers P10, for example, 64 or 128 number of ultrasonic transducers P10.

Examples of the ultrasonic transducer P10 may include a magnetostrictive ultrasonic transducer using a magnetostrictive effect of a magnetic body, a piezoelectric ultrasonic transducer using a piezoelectric effect of a piezoelectric material, and a capacitive micromachined ultrasonic transducer to transmit and receive an ultrasonic wave using vibration of hundreds or thousands of micromachined thin films. In addition, examples of the ultrasonic transducer P10 may include other kinds of transducers to generate an ultrasonic wave according to an electric signal or to generate an electric signal according to an ultrasonic wave.

In an exemplary embodiment, the main body M may further include a beamforming unit 100, an image generation unit 200, a point spread function database 220, a system controller 300, and an image processing unit 320.

The beamforming unit 100 of the main body M receives an ultrasonic signal from the ultrasonic receiver P12 and beamforms the received ultrasonic signal. Specifically, the beamforming unit 100 beamforms a plurality of channel data to estimate the size of a reflected wave in a specific space.

Figure 14:
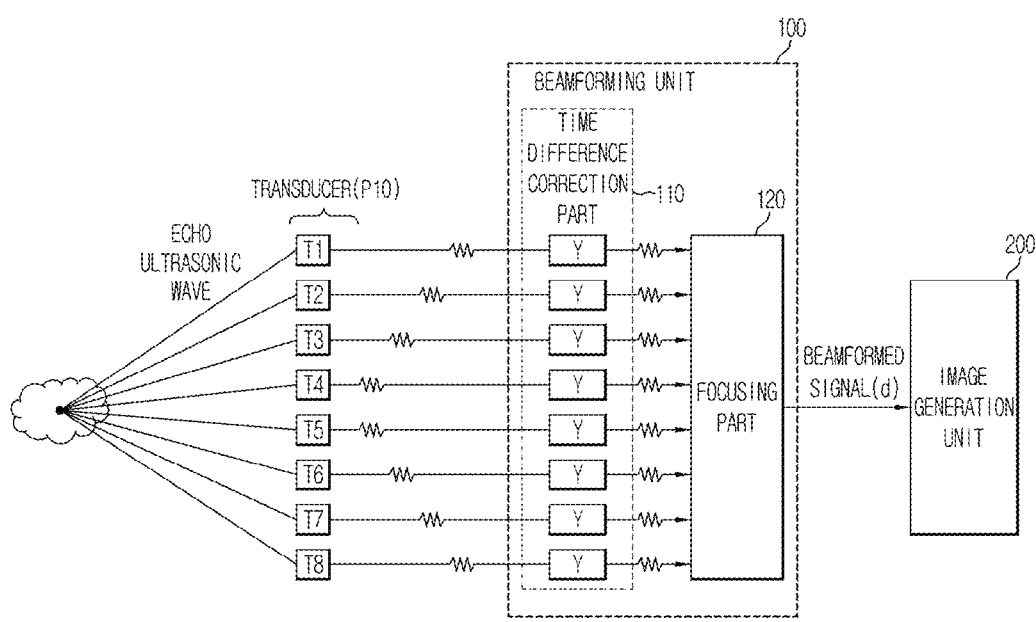
FIG. 14 is a view illustrating an exemplary embodiment of a beamforming unit.

FIG. 14 is a view illustrating an exemplary embodiment of a beamforming unit. As shown in FIG. 14, the beamforming unit 100 may include a time difference correction part 110 and a focusing part 120.

Referring to FIG. 14, echo ultrasonic waves reflected by a target portion ob1 is received by the ultrasonic transducers P10, specifically the ultrasonic receivers P12. However, respective distances between ultrasonic transducers T1 to T6 installed at the ultrasonic probe unit P and the target portion ob1 are different and sound speeds of echo ultrasonic waves are substantially uniform. Even in a case in which the echo ultrasonic waves are reflected by the same target portion ob1, the respective ultrasonic transducers T1 to T6 receive the echo ultrasonic waves from the same target portion ob1 at different times. In other words, ultrasonic signals output by the respective ultrasonic transducers T1 to T6 have predetermined time differences therebetween based on the echo ultrasonic waves reflected by the same target portion ob1. For this reason, time differences among the ultrasonic signals generated by the respective ultrasonic transducers T1 to T6 may be first corrected.

The time difference correction part 110 of the beamforming unit 100 corrects time differences among ultrasonic signals. For example, as shown in FIGS. 13 and 14, the time difference correction part 110 delays transmission of ultrasonic signals input into specific channels to a predetermined extent such that the ultrasonic signals input into the respective channels are transmitted to the focusing part 120 substantially at the same time.

The focusing part 120 of the beamforming unit 100 focuses the ultrasonic signals, of which time differences have been corrected.

The focusing part 120 adds a predetermined weight, i.e. a beamforming coefficient, to each of the input ultrasonic signals to emphasize a signal from a specific position and attenuate a signal from another position and then focuses the ultrasonic signals. As a result, an ultrasonic image based on a user demand or user convenience may be generated.

In this case, the focusing part 120 may focus the ultrasonic signals using a beamforming coefficient irrespective of the ultrasonic signals output by the ultrasonic receivers P12, according to a data independence type beaming forming method. Alternatively, an optimal beamforming coefficient may be calculated based on the input ultrasonic signals and the ultrasonic signals may be focused using the calculated beamforming coefficient, according to an adaptive beamforming method.

The beamforming process may be represented by Equation 2.

$$z[n] = \sum_{m=0}^{M-1} w_m[n]x_m[n - \Delta_m[n]] \quad \text{[Equation 2]}$$

Herein, n is a value representing a position of a target portion ob1, i.e. a specific depth of the target portion ob1, m represents an m-th channel at a position n of the target portion ob1, and $w_m$ represents a beamforming coefficient w added to an ultrasonic signal of the m-th channel. Meanwhile, $\Delta_m$ is a time delay value used in the time difference correction part 110 to delay a transmission time of the ultrasonic signal. According to Equation 2, the focusing part 120 focuses the ultrasonic signals of which time differences therebetween have been corrected, corresponding to the respective channels to output a beamformed ultrasonic signal (d).

As shown in FIGS. 12 and 14, the ultrasonic signal (d) beamformed by the beamforming unit 100 is transmitted to the image generation unit 200.

Figure 15:
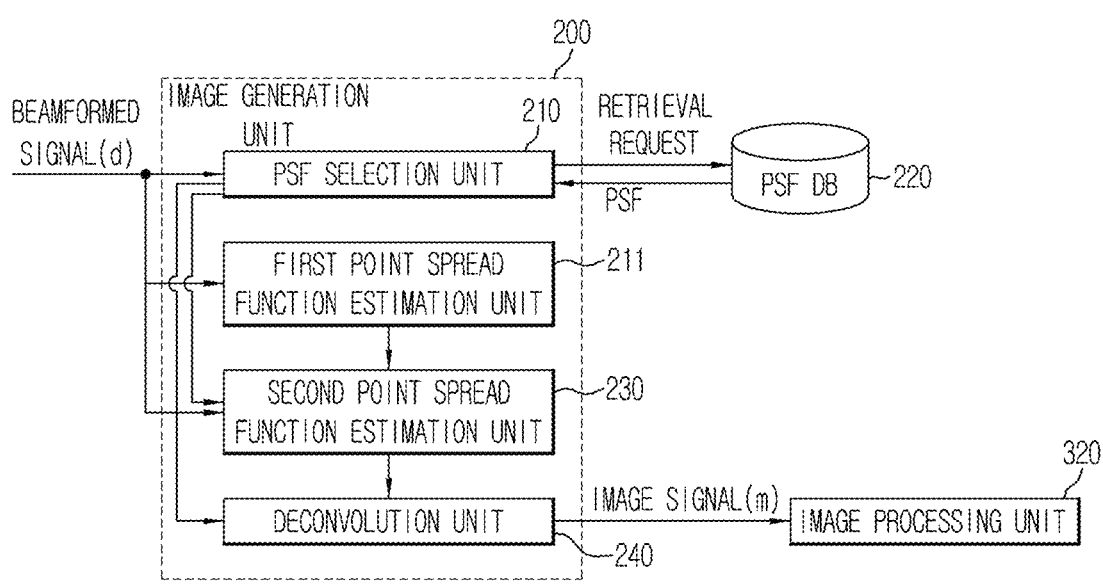
FIG. 15 is a block diagram illustrating an exemplary embodiment of an image generation unit of an ultrasonic imaging apparatus.

FIG. 15 is a block diagram illustrating an exemplary embodiment of an image generation unit of an ultrasonic imaging apparatus.

As shown in FIG. 15, the image generation unit 200 may include a point spread function selection unit 210 and a deconvolution unit 240.

The point spread function selection unit 210 selects at least one point spread function from a point spread function database 220. In this case, the point spread function database 220 may include one-dimensional point spread functions and/or two-dimensional point spread functions.

As described above, factors significantly affecting a point spread function when an ultrasonic image is restored in the ultrasonic imaging apparatus include a speed, i.e. sound speed, of an ultrasonic wave and the distance between a target portion from which the ultrasonic wave is generated or reflected and a collection unit, for example, a depth of a lesion in a human body. The point spread function database 220 may include one-dimensional or two-dimensional point spread functions, which are pre-calculated and measured using situational variables, such as a speed of an ultrasonic wave and a depth of a target portion which significantly affect a point spread function to restore the ultrasonic wave.

In an exemplary embodiment, in a case in which the point spread function selection unit 210 selects a one-dimensional point spread function, the image generation unit 200 may further include a second point spread function estimation unit 230 to estimate a two-dimensional point spread function based on the one-dimensional point spread function selected by the point spread function selection unit 210.

In this case, the point spread function selection unit 210 selects an appropriate one-dimensional point spread function from the point spread function database 220 according to the depth of the target portion ob1 in the object ob or the speed of the ultrasonic wave based on the beamformed signal (d). In this case, the one-dimensional point spread function may be a point spread function in a lateral direction of the target portion ob1.

The second point spread function estimation unit 230 estimates a two-dimensional point spread function based on the one-dimensional point spread function selected by the point spread function selection unit 210. Since point spread functions in an axial direction are not significantly changed according to a sound speed of an ultrasonic wave or a depth of the target portion ob1 as described above, the second point spread function estimation unit 230 may estimate and acquire a two-dimensional point spread function using the one-dimensional point spread function selected by the point spread function selection unit 210, for example, a point spread function in a lateral direction, based on the assumption that one-dimensional point spread functions in the axial direction are substantially uniform.

Figure 16:
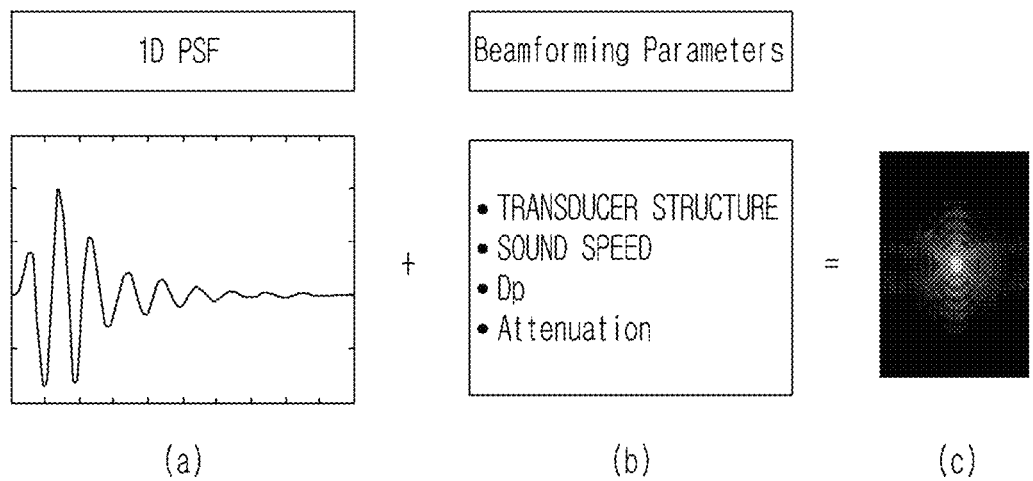
FIG. 16 is a view for explaining a second point spread function.

FIG. 16 is a view for explaining a second point spread function. The second point spread function estimation unit 230 may combine a selected one-dimensional point spread function as shown in FIG. 16(a) and an additional coefficient, such as a second point spread function estimation coefficient, as shown in FIG. 16(b) to estimate a second point spread function as shown in FIG. 16(c).

As shown in FIG. 16, the second point spread function estimation coefficient may be a beamforming coefficient. The beamforming coefficient may be calculated using at least one selected from among the arrangement structure of the ultrasonic transducer P10, a sound speed of an ultrasonic wave, a depth of a target portion, and a signal attenuation rate. On the other hand, the second point spread function estimation coefficient may be at least one selected from among the arrangement structure of the ultrasonic transducer P10, a sound speed of an ultrasonic wave, a depth of a target portion, and signal attenuation rate. To this end, the second point spread function estimation unit 230 may receive the beamformed ultrasonic signal (d) or information regarding the beamformed ultrasonic signal (d) from the beamforming unit 100.

The second point spread function estimation unit 230 may transmit the two-dimensional point spread function estimated as described above to the deconvolution unit 240, which may two-dimensionally deconvolute the beamformed signal (d).

In another exemplary embodiment of the image generation unit 200, the point spread function selection unit 210 may select an appropriate two-dimensional point spread function corresponding to the beamformed ultrasonic signal (d) input from the point spread function database 220.

In this case, at least one two-dimensional point spread function of the point spread function database 220 may be a point spread function actually measured and acquired according to various situational variables based on the assumption that one-dimensional point spread functions in an axial direction are substantially similar to one another.

After selecting and deciding the two-dimensional point spread function, the point spread function selection unit 210 may directly transmit the decided point spread function to the deconvolution unit 240, which may two-dimensionally deconvolute the beamformed signal (d).

In still another embodiment, the image generation unit 200 may include a first point spread function estimation unit 211 and a second point spread function estimation unit 230. The first point spread function estimation unit 211 estimates a one-dimensional point spread function based on the beamformed ultrasonic signal (d) without retrieval from the point spread function database 220.

In this case, the first point spread function estimation unit 211 may estimate a one-dimensional point spread function using at least one filter such as, for example, a minimum least square filter or a cepstrum filter.

The estimated one-dimensional point spread function is transmitted to the second point spread function estimation unit 230. The second point spread function estimation unit 230 estimates a second-dimensional point spread function based on the estimated one-dimensional point spread function. In a similar manner as described above, the second point spread function estimation unit 230 may estimate a second-dimensional point spread function using the one-dimensional point spread function estimated by the first point spread function estimation unit 211 based on the assumption that one-dimensional point spread functions in an axial direction are substantially uniform.

The second point spread function estimation unit 230 transmits the estimated second-dimensional point spread function to the deconvolution unit 240.

The deconvolution unit 240 two-dimensionally deconvolutes the beamformed signal (d) using the second-dimensional point spread function received from the point spread function selection unit 210 or the second point spread function estimation unit 230 to restore an image identical or substantially similar to the ideal image o.

An image signal of the restored image may be transmitted to an image processing unit 320, a storage unit 321, or a display unit dp.

The image processing unit 320 may generate an ultrasonic image which may be identified by a user based on the image generated by the image generation unit 200 or perform a predetermined image processing on the image generated by the image generation unit 200.

In an exemplary embodiment, the image processing unit 320 may generate an ultrasonic image in various modes based on an image signal (m) output from the image generation unit 200. A mode A and a mode B may be used as the ultrasonic image modes. The mode A is a mode to display an ultrasonic image using an amplitude thereof. Specifically, the mode A is a mode to display a target portion t as a distance of the target portion t from the ultrasonic probe unit 10 (or a time interval for arrival of an ultrasonic wave emitted from the ultrasonic probe unit 10) and to display reflection intensity of the ultrasonic wave as an amplitude thereof. The mode B is a mode to display a level of an echo ultrasonic wave as brightness on a screen. In a case in which an ultrasonic image is generated in the mode B, a user may easily and intuitively check tissue or structure in the object ob by using only the ultrasonic image. For this reason, the mode B is generally used. An ultrasonic image in the mode B is shown in FIG. 4C.

In addition, the image processing unit 320 may correct the ultrasonic image generated by the image generation unit 200 according to user's intention or user convenience. For example, the image processing unit 320 may correct brightness, luminance, a contrast, or a color of the ultrasonic image such that a user may clearly see tissue in the ultrasonic image. In a case in which a plurality of ultrasonic images is output from the image generation unit 200, it may be possible to generate a three-dimensional stereoscopic ultrasonic image using the output ultrasonic images.

The storage unit 321 temporarily or continuously stores an image signal generated by the image generation unit 200 and an image signal of an image corrected by the image processing unit 320.

The display unit dp presents an ultrasonic image to a user. According to exemplary embodiments, the display unit dp may display an ultrasonic image deconvoluted by the image generation unit 200 to a user or display a user an ultrasonic image acquired by the image processing unit 320 which performs a predetermined image processing on an image generated by the image generation unit 200. In this case, the ultrasonic image displayed on the display unit dp may be an ultrasonic image in the mode B or a three-dimensional stereoscopic ultrasonic image.

Meanwhile, the main body M of the ultrasonic imaging apparatus may further include an ultrasonic generation controller 310. The ultrasonic generation controller 310 receives a control command from the system controller 300, generates a predetermined pulse signal according to the received control command, and transmits the generated pulse signal to the ultrasonic generator P11. The ultrasonic generator P11 is vibrated according to the received pulse signal to generate an ultrasonic wave. In addition, the ultrasonic generation controller 310 may generate an additional control signal for the power supply unit 311 electrically connected to the ultrasonic generator P11 and transmit the generated control signal to the power supply unit 311. The power supply unit 311 applies a predetermined AC current to the ultrasonic generator P11 according to the received control signal.

The system controller 300 controls operations of the ultrasonic probe unit P, the beamforming unit 100, the image generation unit 200, the image processing unit 320, the storage unit 321, and the display unit dp.

According to exemplary embodiments, the system controller 300 may generate a predetermined control command for the ultrasonic probe unit P, etc. according to a predetermined setting or a user instruction or command input through an additional input unit i.

The input unit i receives a user instruction or command to control the ultrasonic imaging apparatus. The input unit i may include various user interfaces, such as a keyboard, a mouse, a trackball, a touchscreen, and a paddle. Alternatively, the input unit i may be a workstation connected to the main body M.

In an exemplary embodiment of the ultrasonic imaging apparatus described above, the ultrasonic transducer P10 may be installed at the ultrasonic probe unit P and the beamforming unit 100, the image generation unit 200, the ultrasonic generation controller 310, and the image processing unit 320 may be installed at the main body M. According to alternative embodiments, some of components installed at the main body M may be provided at the ultrasonic probe unit P.

Hereinafter, various exemplary embodiments of an ideal image restoration method based on an input image will be described with reference to FIGS. 17 to 19.

Figure 17:
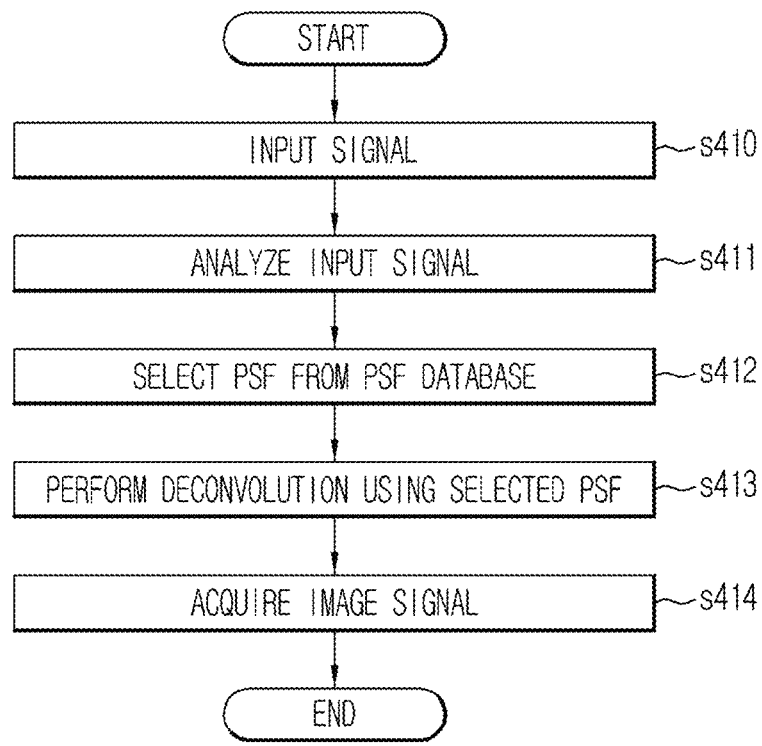
FIGS. 17 to 19 are flowcharts illustrating various exemplary embodiments of an ideal image restoration method based on an input image.

FIG. 17 is a flowchart illustrating an exemplary embodiment of an image generation method using a point spread function. As shown in FIG. 17, a signal (d) is input first. In an exemplary embodiment, the input signal (d) may be a beamformed signal, such as a beamformed ultrasonic signal, of the ultrasonic imaging apparatus (s410).

Next, the input signal (d) is analyzed (s411). In this case, meta information additionally added to the input signal (d) may be used to analyze the input signal (d). The input signal (d) may be analyzed based on a situational variable, such as a sound speed of an ultrasonic wave used to acquire the input signal (d) or the distance between the data collection unit and a target portion ob1, for example, a depth of the target portion ob1.

An appropriate two-dimensional point spread function is selected according to the analysis result of the input signal (d). The selected two-dimensional point spread function may be at least one selected from among a plurality of point spread functions stored in the point spread function database 12.

The selected two-dimensional point spread function is called from the point spread function database 12 (s412). The point spread functions stored in the point spread function database 12 may be point spread functions pre-measured according to a situational variable, such as a sound speed of an ultrasonic wave or the distance between the data collection unit and a target portion ob1, as shown in FIG. 6.

Two-dimensional deconvolution is performed on the input signal (d) using the selected two-dimensional point spread function (s413). As a result, an image signal (m) identical or substantially similar to an ideal image is acquired and output (s414).

Figure 18:
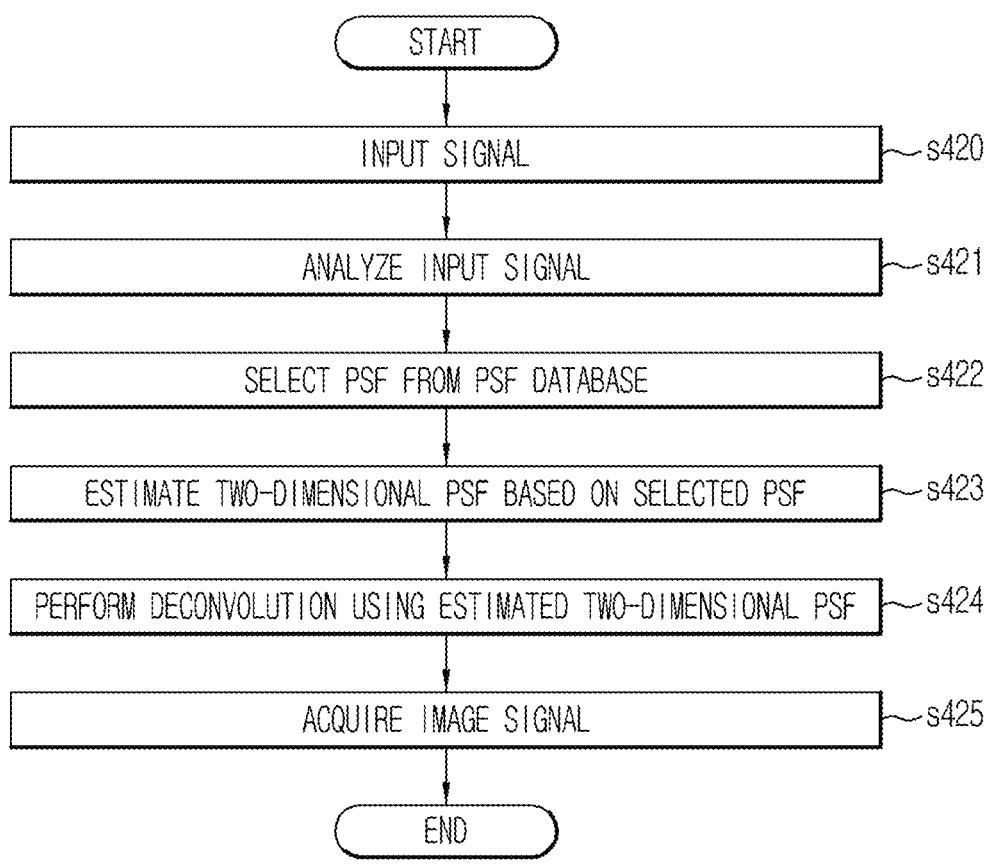

FIG. 18 is a flowchart illustrating another exemplary embodiment of an image generation method using a point spread function. Referring to FIG. 18, a signal (d) is input (s420). The input signal (d) is analyzed (s421) In the same manner as described above. The input signal (d) may be a beamformed signal. In addition, the input signal (d) may be analyzed based on the situational variable as described above. For example, the situational variable may be a sound speed of an ultrasonic wave or a depth of a target portion.

An appropriate one-dimensional point spread function is selected according to the analysis result of the input signal (d). The selected one-dimensional point spread function may be at least one point spread function stored in the point spread function database 12. In an exemplary embodiment, the point spread function stored in the point spread function database 12 may be a one-dimensional point spread function pre-measured according to a situational variable, such as a sound speed of an ultrasonic wave or the distance between the data collection unit and a target portion ob1. For example, the one-dimensional point spread function may be a point spread function in a lateral direction. The selected one-dimensional point spread function is called from the point spread function database 12 (s422).

A two-dimensional point spread function is estimated using the called point spread function. Since a point spread function in an axial direction is not significantly changed according to a sound speed of an ultrasonic wave or a distance as described above, the two-dimensional point spread function may be estimated based on the point spread function in the lateral direction (s423).

Meanwhile, according to exemplary embodiments, a second point spread function estimation variable pre-defined to estimate the two-dimensional point spread function or selected by a user may be used. For example, the second point spread function estimation variable may be a beamforming coefficient. More specifically, the second point spread function estimation variable may be a variable, such as a sound speed of an ultrasonic wave, a change of a sound speed, a distance from a target portion in an object, an arrangement form of an input signal generation module for generating the input signal, or an attenuation rate of an input signal per channel.

Deconvolution is performed on the input signal (d) using the estimated two-dimensional point spread function (s424) to restore an image. Next, an image signal of the restored image is acquired (s425).

Figure 19:
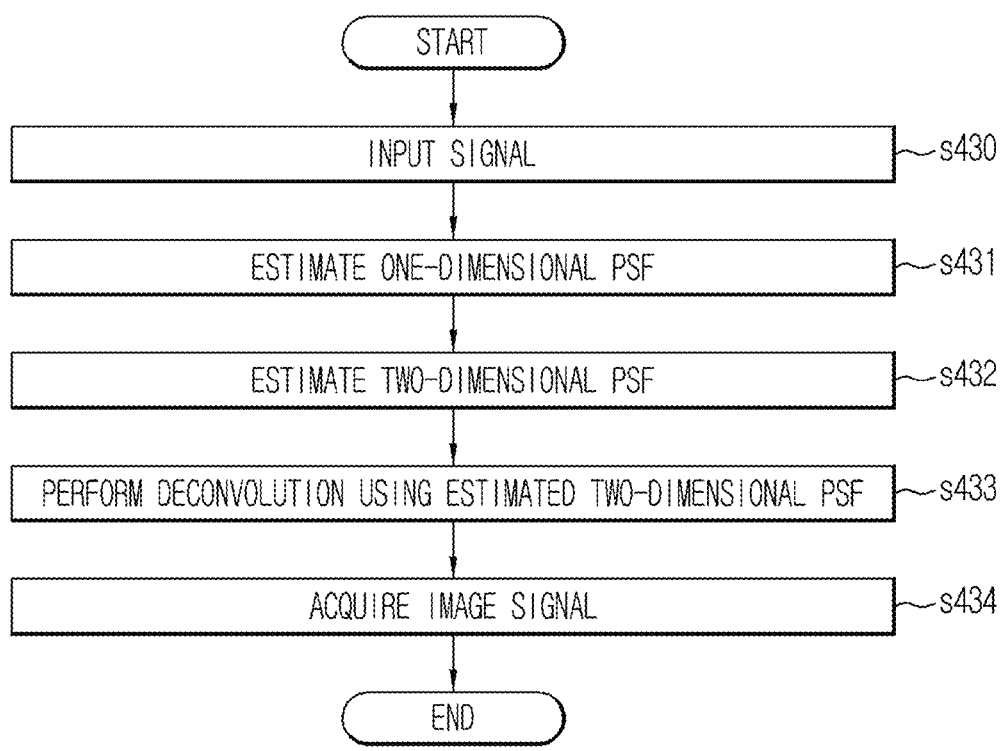

FIG. 19 is a flowchart illustrating still another exemplary embodiment of an image generation method using a point spread function. As shown in FIG. 19, a signal (d) is input first (s430). The input signal (d) may be a beamformed signal as described above.

A one-dimensional point spread function is estimated according to the analysis result of the input signal (d) (s431). Here, a one-dimensional point spread function may be estimated with respect to the input signal (d) using at least one filter. A minimum least square filter or a cepstrum filter may be used.

When the one-dimensional point spread function is estimated as described above, a two-dimensional point spread function is estimated based on the estimated one-dimensional point spread function (s432). In this case, the two-dimensional point spread function may be estimated in a manner similar to in the exemplary embodiment described with reference to FIG. 18.

When the two-dimensional point spread function is acquired, two-dimensional deconvolution is performed on the input signal (d) using the acquired two-dimensional point spread function (s433). As a result, an image is restored and an image signal (m) of the restored image is acquired (s434).

Hereinafter, various exemplary embodiments of a control method of the ultrasonic imaging apparatus will be described with reference to FIGS. 20 to 22.

Figure 20:
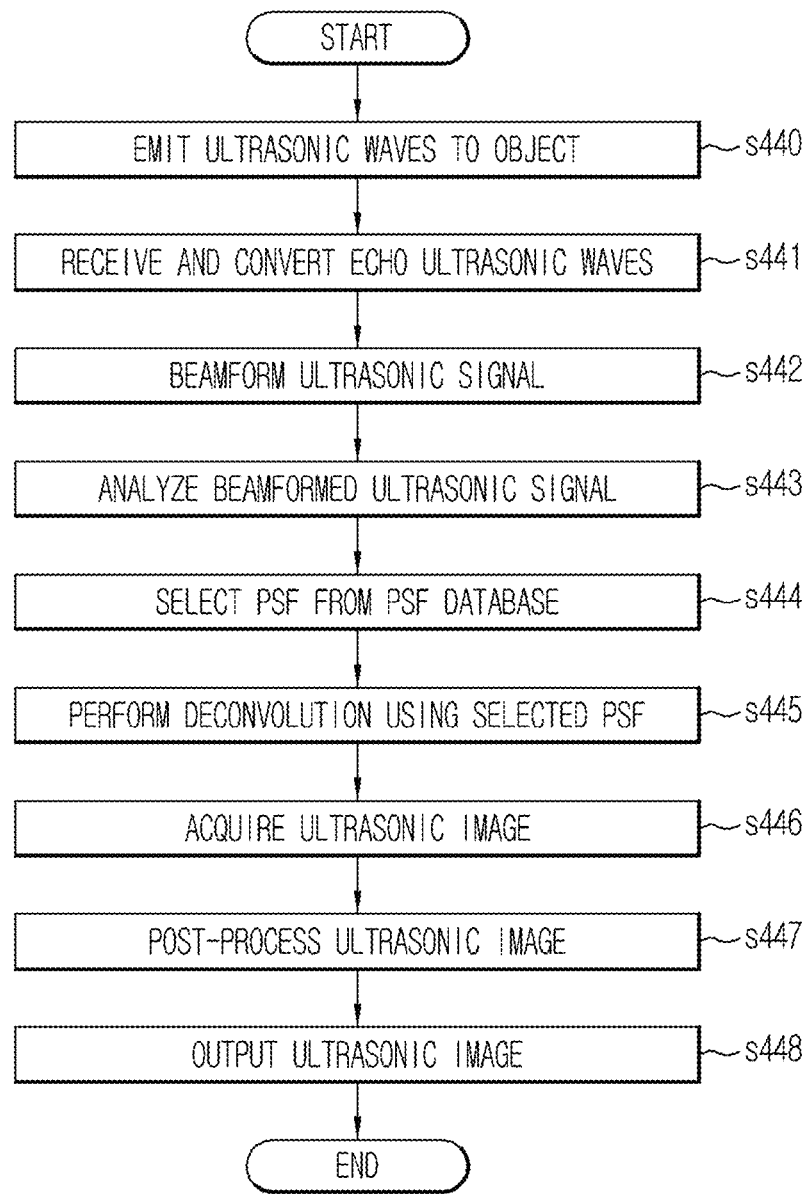
FIGS. 20 to 22 are flowcharts illustrating various exemplary embodiments of a control method of an ultrasonic imaging apparatus.

FIG. 20 is a flowchart illustrating an exemplary embodiment of a control method of an ultrasonic imaging apparatus. As shown in FIG. 20, the ultrasonic probe unit P of the ultrasonic imaging apparatus emits ultrasonic waves to a target portion ob1 of an object (s440). The target portion ob1 fully or partially reflects the emitted ultrasonic waves. The ultrasonic probe unit P receives the reflected ultrasonic waves, i.e. echo ultrasonic waves, and converts the received ultrasonic waves into electric signals to output ultrasonic signals (s441).

Time differences among the output ultrasonic signals are corrected and the ultrasonic signals are focused to beamform an ultrasonic signal (s442). The beamformed ultrasonic signal is analyzed (s443) and a point spread function adapted to the beamformed ultrasonic signal (d) is selected.

In this case, a situational variable, such as a sound speed of the ultrasonic wave or a depth of the target portion ob1, may be used to analyze the beamformed ultrasonic signal (d). To analyze the beamformed ultrasonic signal (d), various kinds of information added to the ultrasonic signal (d) as well as the beamformed ultrasonic signal (d) may be used. According to the result of analysis, the sound speed of the ultrasonic wave used to acquire the ultrasonic signal and the depth of the target portion ob1 may be decided.

According to the analysis result, an appropriate point spread function is selected. The selected point spread function may be stored in the point spread function database 220. For example, when the sound speed of the ultrasonic wave used to acquire the ultrasonic signal and the depth of the target portion ob1 are decided according to analysis, a point spread function corresponding to the decided sound speed and depth is selected from the point spread function database 220 as shown in FIG. 6. The point spread function is called from the point spread function database 220 (s444).

The beamformed ultrasonic signal (d) is two-dimensionally deconvoluted using the called point spread function (s445). As a result, an ultrasonic image is restored and acquired (s446). Image post-processing is performed on the restored and acquired ultrasonic image to adjust brightness or contrast of the image as needed (s447) and the image-processed ultrasonic image is output to the display device dp such as, for example, a monitor (s448).

Figure 21:
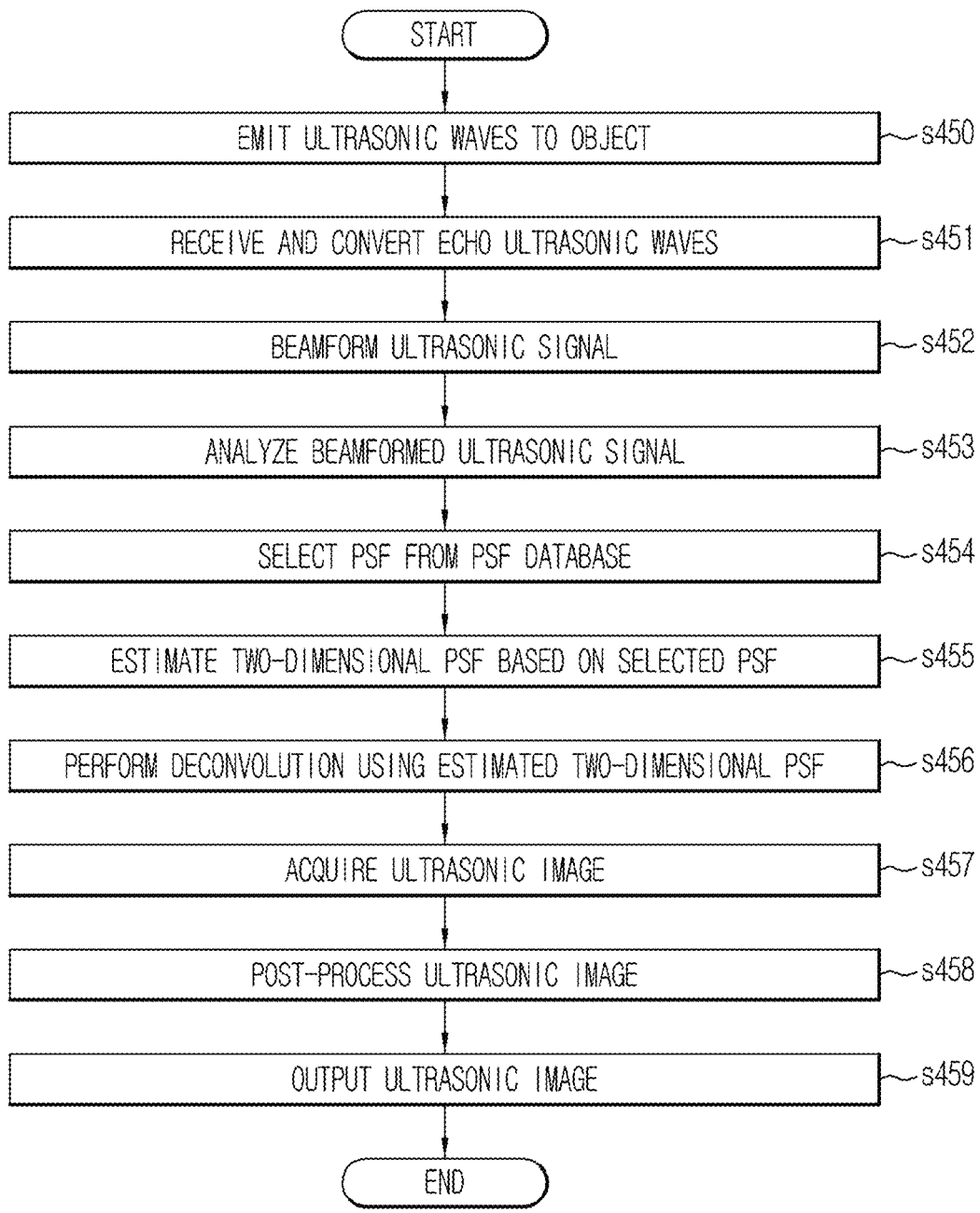

FIG. 21 is a flowchart illustrating another exemplary embodiment of a control method of an ultrasonic imaging apparatus. As shown in FIG. 21, the ultrasonic probe unit P emits ultrasonic waves to a target portion ob1 of an object (s450), receives echo ultrasonic waves reflected by the target portion ob1, and converts the received ultrasonic waves into ultrasonic signals (s451). Next, beamforming, such as time difference correction and focusing, is performed on the ultrasonic signals (s452).

The beamformed ultrasonic signal is analyzed (s453) and an appropriate one-dimensional point spread function is selected according to the analysis result. The one-dimensional point spread function may be a point spread function stored in the point spread function database 220. In addition, information regarding the position of the target portion ob1, such as the depth of the target portion ob1 in the object ob, for example, the depth of a lesion in a human body, may be used to select an appropriate one-dimensional point spread function. In addition, information regarding the ultrasonic wave generated by the ultrasonic probe unit or the sound speed of the received echo ultrasonic wave may also be used. Meanwhile, the selected point spread function may be a point spread function in a lateral direction (s454).

A two-dimensional point spread function is estimated based on the one-dimensional point spread function (s455). Since point spread functions in an axial direction are substantially approximate to each other with respect to a sound speed of an ultrasonic wave as described above, the two-dimensional point spread function is calculated and estimated using the selected point spread function in the lateral direction based on the assumption that a point spread function in the axial direction to actually restore an image is identical to a predetermined point spread function in the axial direction.

In an exemplary embodiment, the two-dimensional point spread function may be estimated using a two-dimensional point spread function estimation variable, which is predefined or selected by a user, for example, a beamforming coefficient. A sound speed of an ultrasonic wave, a change of a sound speed, a distance from a target portion in an object, an arrangement form of an input signal generation module for generating the input signal, or an attenuation rate of an input signal per channel may be used as the two-dimensional point spread function estimation variable.

The beamformed ultrasonic signal (d) is two-dimensionally deconvoluted using the two-dimensional point spread function (s456) to restore an ultrasonic image (s457). The restored ultrasonic image is corrected by predetermined image post-processing (s458) and is output to the display device (s459).

Figure 22:
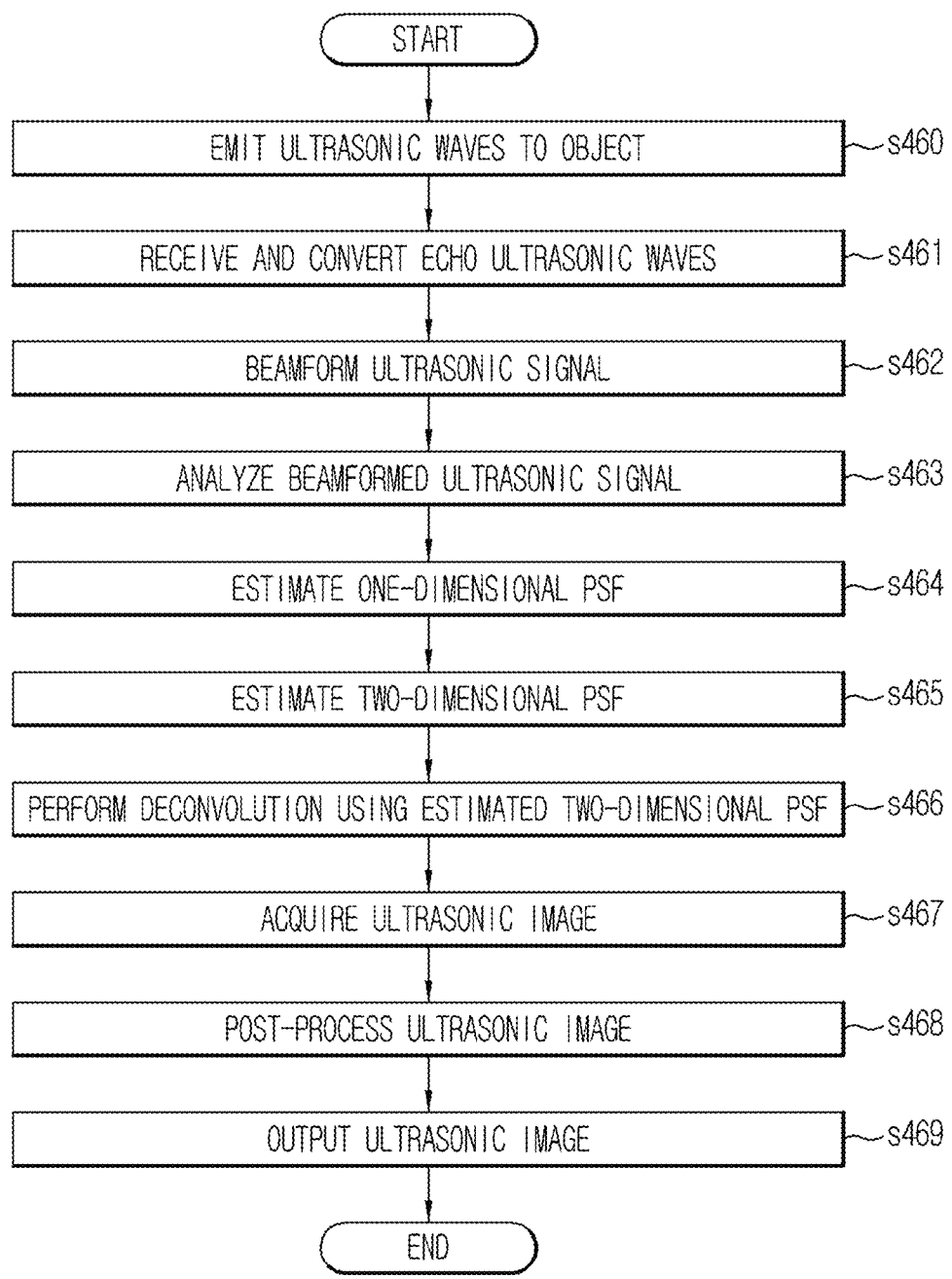

FIG. 22 is a flowchart showing still another exemplary embodiment of a control method of an ultrasonic imaging apparatus. As shown in FIG. 22, the ultrasonic probe unit P emits ultrasonic waves to a target portion ob1 of an object (s460), receives echo ultrasonic waves reflected by the target portion ob1, and converts the received ultrasonic waves into ultrasonic signals (s461). Next, beamforming, such as time difference correction and focusing, is performed on the ultrasonic signals (s462), as described above.

The beamformed ultrasonic signal (d) is analyzed (s463) to estimate a one-dimensional point spread function for the beamformed ultrasonic signal (d) (s464). The one-dimensional point spread function may be estimated using at least one filter, such as a least square filter or a cepstrum filter. Alternatively, various conventional methods may be used to estimate the one-dimensional point spread function. Here, a one-dimensional point spread function in an axial direction may not be estimated but a one-dimensional point spread function in a lateral direction may be estimated.

A two-dimensional point spread function is estimated based on the estimated one-dimensional point spread function (s465). As described above, the two-dimensional point spread function is calculated and estimated using the estimated point spread function in the lateral direction based on the assumption that a point spread function in the axial direction to actually restore an image is substantially identical to a predetermined point spread function in the axial direction. In this case, the two-dimensional point spread function estimation variable as described above may be used to estimate the two-dimensional point spread function.

The beamformed ultrasonic signal (d) is two-dimensionally deconvoluted using the two-dimensional point spread function (s466). As a result, an ultrasonic image identical or substantially similar to an ideal image o is restored (s467). The restored ultrasonic image may be corrected by predetermined image post-processing (s468). The restored or post-processed ultrasonic image is output to the display device (s469).

As described above, in an image processing module, an ultrasonic imaging apparatus using the image processing module, and an ultrasonic image generation method using the ultrasonic imaging apparatus according to exemplary embodiments, an appropriate point spread function may be decided when restoring an image, for example, by generating an image based on an ultrasonic signal.

Also, a point spread function may be promptly decided during generation of an ultrasonic image performed by the ultrasonic imaging apparatus, thereby improving restoring a speed of an ultrasonic image and thus promptly generating an ultrasonic image.

In addition to prompt generation of an ultrasonic image, an appropriate point spread function may be decided, thereby generating an ultrasonic image of high resolution.

A two-dimensional point spread function may be acquired at a higher speed based on a one-dimensional point spread function such that an ultrasonic image of a higher resolution and a higher quality may be acquired.

Thus, a user, such as a doctor or an ultrasonic inspector, may more diagnose a patient using an accurate ultrasonic image acquired promptly by the ultrasonic imaging apparatus.

In addition, a method of deciding a point spread function may be applied to a radar or acoustic signal processing, thereby improving an operation of a radar or acoustic signal processing apparatus according to exemplary embodiments.

Although a few embodiments of the disclosure have been shown and described, it would be appreciated by those skilled in the art that changes may be made in these embodiments without departing from the principles and spirit of the disclosure, the scope of which is defined in the claims and their equivalents.

What is claimed is:

1. An ultrasonic imaging apparatus comprising:
a beamformer implemented by at least one processor, the beamformer configured to beamform an input signal generated from a first ultrasonic wave reflected from a target and to output a beamformed signal based on the input signal;
a point spread function (PSF) database storing a plurality of point spread functions acquired through previous measurements according to respective speeds of a second ultrasonic wave; and
an image generator implemented by the at least one processor, the image generator configured to:
analyze the beamformed signal to obtain a speed of the first ultrasonic wave used to acquire the input signal;
select a point spread function from among the plurality of point spread functions stored in the point spread function database, the selected point spread function having been acquired through previous measurement at a speed of the second ultrasonic wave corresponding to the obtained speed of the first ultrasonic wave used to acquire the input signal;
perform deconvolution on the beamformed signal using the selected point spread function; and
obtain an image of the target according to a result of the deconvolution,
wherein the point spread function (PSF) database comprises one-dimensional point spread functions or two-dimensional point spread functions pre-calculated and measured using the respective speeds of the second ultrasonic wave.

2. The ultrasonic imaging apparatus according to claim 1, wherein the plurality of point spread functions are acquired through previous measurements according to the respective speeds of the second ultrasonic wave and depths of a portion from an image data collection unit, and
wherein the image generator is configured to select the point spread function from among the plurality of point spread functions stored in the point spread function database, the selected point spread function having been acquired through:
previous measurement at the speed of the second ultrasonic wave corresponding to the obtained speed of the first ultrasonic wave, and
a depth of the portion from the image data collection unit corresponding to a depth of the target.

3. The ultrasonic imaging apparatus according to claim 2, wherein the image generator arranges the beamformed signal based on the speed of the first ultrasonic wave used to acquire the input signal and the depth of the portion from the image data collection unit and selects the point spread function from the point spread function database based on a result of the arrangement.

4. An ultrasonic imaging apparatus comprising:
a beamformer implemented by at least one processor, the beamformer configured to output a beamformed signal based on an input signal, the input signal being generated from a first ultrasonic wave reflected from a target portion of an object; and
an image generator implemented by the at least one processor, the image generator configured to:
analyze the beamformed signal to obtain a speed of the first ultrasonic wave used to acquire the input signal;
select a first point spread function (PSF) from among a plurality of point spread functions stored in a point spread function database, the plurality of point spread functions in the point spread function database having been acquired through previous measurements according to respective speeds of a second ultrasonic wave and the selected first point spread function having been acquired through previous measurement at a speed of the second ultrasonic wave corresponding to the obtained speed of the first ultrasonic wave used to acquire the input signal;
estimate a second point spread function based on the selected first point spread function, to perform deconvolution using the beamformed signal and the estimated second point spread function; and
obtain an image of the target portion of the object according to a result of the performed deconvolution,
wherein the point spread function database (PSF) comprises one-dimensional point spread functions or two-dimensional point spread functions pre-calculated and measured using the respective speeds of the second ultrasonic wave.

5. The ultrasonic imaging apparatus according to claim 4, wherein the plurality of point spread functions stored in the point spread function database are acquired through previous measurements according to the respective speeds of the second ultrasonic wave and depths of a portion from an image data collection unit, and
wherein the image generator is configured to select the first point spread function from among the plurality of point spread functions, the first point spread function having been acquired through:
previous measurement at the speed of the second ultrasonic wave corresponding to the speed of the first ultrasonic wave used to acquire the input signal, and
a depth of the portion from the image data collection unit corresponding to a depth of the target portion of the object.

6. The ultrasonic imaging apparatus according to claim 5, wherein the image generator arranges the beamformed signal based on the speed of the first ultrasonic wave used to acquire the input signal and the depth of the target portion from the image data collection unit and selects the first point spread function from the point spread function database based on a result of the arrangement.

7. The ultrasonic imaging apparatus according to claim 4, wherein the image generator estimates the second point spread function using the first point spread function and again using the beamformed signal.

8. The ultrasonic imaging apparatus according to claim 4, wherein the image generator estimates the second point spread function using the first point spread function and at least one second point spread function estimation variable.

9. The ultrasonic imaging apparatus according to claim 8, wherein the at least one second point spread function estimation variable comprises a beamforming coefficient.

10. The ultrasonic imaging apparatus according to claim 8, wherein the at least one second point spread function estimation variable comprises at least one of a sound speed of a ultrasonic wave, a change of the sound speed thereof, a location of the target portion of the object, an arrangement form of an input signal generation module for generating the input signal, and an attenuation rate of the input signal per channel.

11. An image generation method using an ultrasonic image apparatus, the method comprising:
- emitting ultrasonic waves to a target portion of an object, receiving echo ultrasonic waves reflected by the target portion of the object, and converting the received echo ultrasonic waves into ultrasonic signals;
- outputting an ultrasonic signal beamformed based on the ultrasonic signals;
- analyze the beamformed ultrasonic signal to obtain a speed of the echo ultrasonic waves used to acquire the ultrasonic signals;
- selecting a point spread function (PSF) from among a plurality of point spread functions stored in a point spread function database, the plurality of point spread functions in the point spread function database having been acquired through previous measurements according to respective speeds of an ultrasonic wave and the selected point spread function having been acquired through previous measurement at a speed of the ultrasonic wave corresponding to the obtained speed of the echo ultrasonic waves used to acquire the ultrasonic signals;
- performing deconvolution on the beamformed ultrasonic signal using the selected point spread function; and
- obtaining an image of the target portion of the object according to a result of the deconvolution, wherein the point spread function (PSF) database comprises one-dimensional point spread functions or two-dimensional point spread functions pre-calculated and measured using the respective speeds of the ultrasonic wave.

12. The image generation method according to claim 11, wherein the plurality of point spread functions stored in the point spread function database are acquired through previous measurements according to the respective speeds of the ultrasonic wave and depths of a portion from an image data collection unit, and
wherein the selecting comprises selecting the point spread function from among the plurality of point spread functions, the selected point spread function having been acquired through:
- previous measurement at the speed of the ultrasonic wave corresponding to the obtained speed of the echo ultrasonic waves used to acquire the ultrasonic signals, and
- the depth of the portion from the image data collection unit corresponding to a depth of the target portion of the object.

13. The image generation method according to claim 12, wherein the selecting comprises arrangement the beamformed ultrasonic signal based on the speed of the echo ultrasonic waves of the ultrasonic signals and the depth of the target portion from the image data collection unit and selecting the point spread function from the point spread function database based on a result of the arrangement.

* * * * *